United States Patent
Kujala et al.

(10) Patent No.: US 11,534,753 B2
(45) Date of Patent: Dec. 27, 2022

(54) MICROFLUIDIC KIDNEY-ON-CHIP

(71) Applicant: EMULATE, Inc., Boston, MA (US)

(72) Inventors: Ville Kujala, Medford, MA (US); Hyoungshin Park, Newton, MA (US); Sonalee Barthakur, Boston, MA (US); Sauveur Jeanty, Boston, MA (US); Brian Zuckerman, Cambridge, MA (US); Josiah Sliz, Boston, MA (US); Tanvi Shroff, Cambridge, MA (US); Geraldine A Hamilton, Boston, MA (US); Kyung-Jin Jang, Boston, MA (US); Ananth Nookala, Boston, MA (US); Gang Luo, Boston, MA (US); Donald Mckenzie, Boston, MA (US)

(73) Assignee: EMULATE, INC., Boston, MA (US)

( * ) Notice: Subject to any disclaimer, the term of this patent is extended or adjusted under 35 U.S.C. 154(b) by 254 days.

(21) Appl. No.: 16/352,234

(22) Filed: Mar. 13, 2019

(65) Prior Publication Data
US 2020/0269234 A1     Aug. 27, 2020

Related U.S. Application Data

(63) Continuation-in-part of application No. PCT/US2019/019250, filed on Feb. 22, 2019.

(51) Int. Cl.
*B01L 3/00* (2006.01)
*C12M 3/06* (2006.01)
(Continued)

(52) U.S. Cl.
CPC ........... *B01L 3/5027* (2013.01); *C12M 23/16* (2013.01); *C12Q 1/6809* (2013.01); *G01N 33/5023* (2013.01); *G01N 33/5064* (2013.01); *G01N 33/5091* (2013.01); *B01L 2300/0819* (2013.01); *B01L 2400/0487* (2013.01); *C12M 25/02* (2013.01)

(58) Field of Classification Search
CPC ........... B01L 3/5027; B01L 2300/0819; B01L 2400/0487; C12M 23/16; C12M 25/02; G01N 33/5023; G01N 33/5064; G01N 33/5091; C12Q 1/6809
See application file for complete search history.

(56) References Cited

U.S. PATENT DOCUMENTS

| 2007/0048727 | A1* | 3/2007 | Shuler | C12M 23/16 435/1.2 |
| 2016/0243738 | A1 | 8/2016 | Katrycz | 264/294 |

FOREIGN PATENT DOCUMENTS

| WO | WO/2010/009307 | 1/2010 |
| WO | WO/2012/118799 | 9/2012 |

(Continued)

OTHER PUBLICATIONS

Vedula et al., A microfluidic renal proximal tubule with active reabsorption function, Oct. 11, 2017, PLoS One, vol. 12, p. 1-15 (Year: 2017).*

(Continued)

*Primary Examiner* — Christine T Mui
*Assistant Examiner* — Kathryn Elizabeth Limbaugh
(74) *Attorney, Agent, or Firm* — Medlen & Carroll, LLP

(57) ABSTRACT

The present invention relates to microfluidic fluidic devices, methods and systems as microfluidic kidney on-chips, e.g. human Proximal Tubule-Chip.

17 Claims, 12 Drawing Sheets

(51) Int. Cl.
*C12Q 1/6809* (2018.01)
*G01N 33/50* (2006.01)
*C12M 1/12* (2006.01)

(56) References Cited

FOREIGN PATENT DOCUMENTS

| WO | WO/2013/086486 | 6/2013 |
|---|---|---|
| WO | WO/2013/086502 | 6/2013 |
| WO | WO/2014/210364 | 12/2014 |
| WO | WO/2015/013332 | 1/2015 |
| WO | WO/2015/138032 | 9/2015 |
| WO | WO/2015/138034 | 9/2015 |

OTHER PUBLICATIONS

Vedula et al., A microfluidic renal proximal tubule with active reabsorptive function, Oct. 11, 2017, PLoS ONE, 12(10): e0184330, pp. 1-15. (Year: 2017).*
Maschmeyer et al. A four-organ-chip for interconnected long-term co-culture of humane intestin, liver, skin and kidney equivalents, 2015, Lab on a Chip, 15, pp. 2688-2699. (Year: 2015).*
Wilmer et al., Kidney-on-a-Chip Technology for Drug-Induced Nephrotoxicity Screening, Feb. 2016, Trends in Biotechnology, vol. 34, No. 2, pp. 156-170. (Year: 2016).*
U.S. Appl. No. 61/810,944.
U.S. Appl. No. 61/839,702, filed Jun. 26, 2013, Ingber, D. E. et al.
Barry, R. A. et al. (2009) "Direct-Write Assembly of 3D Hydrogel Scaffolds for Guided Cell Growth," *Advanced Materials* 21(23), 2407-2410.
Benjamini, Y. et al. (1995) "Controlling the False Discovery Rate: A Practical and Powerful Approach to Multiple Testing," *Journal of the Royal Statistical Society. Series B* 57(1), 289-300.
Bischel, L. L. et al. (2012) "A Practical Method for Patterning Lumens through ECM Hydrogels via Viscous Finger Patterning," *Journal of Laboratory Automation* 17(2), 96-103.
Hanson-Shepherd, J. N. et al. (2011) "3D Microperiodic Hydrogel Scaffolds for Robust Neuronal Cultures," *Advanced Functional Materials* 21(1), 47-54.
Kamiguchi, N. et al. (2010) "A 96-Well Plate Assay for CYP4503A Induction Using Cryopreserved Human Hepatocytes," *Drug Metabolism and Disposition* 38(11), 1912.
Sun, L. et al. (2012) "Direct-Write Assembly of 3D Silk/Hydroxyapatite Scaffolds for Bone Co-Cultures," *Advanced Healthcare Materials* 1(6), 729-735.
Thangawng, A. L. et al. (2007) "An ultra-thin PDMS membrane as a bio/micro-nano interface: fabrication and characterization," *Biomedical Microdevices* 9(4), 587-595.
Whitesides, G. M. et al. (2001) "Soft Lithography in Biology and Biochemistry," *Annual Review of Biomedical Engineering* 3(1), 335-373.
Wu, W. et al. (2011) "Omnidirectional Printing of 3D Microvascular Networks," *Advanced Materials* 23(24), H178-H183.
Wu, W. et al. (2010) "Directwrite assembly of biomimetic microvascular networks for efficient fluid transport," *Soft Matter* 6, 739-742.
Zhang, B. et al. (2017) "Organ-on-a-chip devices advance to market," *Lab on a Chip* 17(14), 2395-2420.

* cited by examiner

MICROFLUIDIC KIDNEY-ON-CHIP

FIELD OF THE INVENTION

The present invention relates to microfluidic fluidic devices, methods and systems as microfluidic kidney on-chips, e.g. human Proximal Tubule-Chip.

BACKGROUND

The kidney plays a key role in elimination of xenobiotics and endogenous compounds through its complicated and efficient uptake and efflux transporting systems. Thus, drug interactions with renal tubular transporters should be investigated systematically to increase our understanding of drug disposition and toxicity, and for predicting potential drug-drug interactions in human.

However, currently available cell-based models often fail to predict renal transporter activity and are not scalable to a predictive clinical outcome due to in vitro-in vivo discrepancy.

Therefore, new ways to assess renal transporter-based drug-drug interactions and tests for drug-associated kidney toxicities are needed.

SUMMARY OF THE INVENTION

The present invention relates to microfluidic fluidic devices, methods and systems as microfluidic kidney on-chips, e.g. human Proximal Tubule-Chip.

In one embodiment, the present invention provides a microfluidic device, comprising a membrane (or other porous or semi-porous barrier), said membrane comprising a first surface and a second surface, said first surface comprising proximal tubule cells and said second surface comprising glomerular microvascular endothelial cells. In one embodiment, said proximal tubule cells are human primary proximal tubular epithelial cells. In one embodiment, said membrane contains pores (which allows for fluidic communication). In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. The microchannels can connect other components (such as reservoirs), i.e., keep components in communication and more particularly, in fluidic communication. The microchannels can be in fluidic communication with each other. In one embodiment, said human primary proximal tubular epithelial cells express tight junction protein ZO-1. In one embodiment, said human primary proximal tubular epithelial cells express beta-catenin. In one embodiment, said human primary proximal tubular epithelial cells express occludin. In one embodiment, said human primary proximal tubular epithelial cells express aquaporin 1 (AQP1). In one embodiment, said human primary proximal tubular epithelial cells express Na/K-ATPase. In one embodiment, said human primary proximal tubular epithelial cells comprise cilia. In one embodiment, said human primary proximal tubular epithelial cells comprise express one or more uptake and efflux transporters. In one embodiment, said endothelial cells express VE-Cadherin.

In one embodiment, the present invention provides a method of culturing, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; and b) culturing said cells under continuous flow of media. In one embodiment, said proximal tubule cells are human primary proximal tubular epithelial cells. In one embodiment, said membrane contains pores. In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. In one embodiment, said human primary proximal tubular epithelial cells express tight junction protein ZO-1. In one embodiment, said human primary proximal tubular epithelial cells express beta-catenin. In one embodiment, said human primary proximal tubular epithelial cells express occludin. In one embodiment, said human primary proximal tubular epithelial cells express aquaporin 1 (AQP1). In one embodiment, said human primary proximal tubular epithelial cells express Na/K-ATPase. In one embodiment, said human primary proximal tubular epithelial cells comprise cilia. In one embodiment, said human primary proximal tubular epithelial cells comprise express one or more uptake and efflux transporters. In one embodiment, said endothelial cells express VE-Cadherin.

In one embodiment, the present invention provides a method of measuring transport, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; b) culturing said cells under continuous flow of media; c) introducing an agent; and d) detecting transport of said agent. In one embodiment, said transport detected in step d) comprises transcellular transport. In one embodiment, said proximal tubule cells are human primary proximal tubular epithelial cells. In one embodiment, said membrane contains pores. In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. In one embodiment, said transport detected in step d) comprises transporter-mediated secretion from the second channel to the first channel.

In one embodiment, the present invention provides a method of measuring toxicity, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; b) culturing said cells under continuous flow of media; c) introducing an agent; and d) detecting toxicity of said agent. In one embodiment, said detecting comprises measuring release of a compound from said cells. In one embodiment, said compound comprises Lactate dehydrogenase (LDH).

In one embodiment, the present invention provides a method of measuring clearance, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; b) culturing said cells under continuous flow of media; c) introducing an agent; and d) detecting clearance of said agent. In one embodiment, said agent is a drug or candidate drug.

BRIEF DESCRIPTION OF THE DRAWINGS

Exemplary embodiments are illustrated in referenced figures. It is intended that the embodiments and figures disclosed herein are to be considered illustrative rather than restrictive.

The file of this patent contains at least one drawing executed in color. Copies of this patent with color drawings will be provided by the Patent and Trademark Office upon request and payment of the necessary fee.

FIG. 4A shows exemplary microscopic images demonstrating a defined and orderly expression of the epithelial tight junction protein ZO-1 (upper right, green) and the endothelial adherent protein VE-Cadherin (lower right, green). Nuclei staining is colored blue.

FIG. 4B shows exemplary microscopic images of proximal tubule cells demonstrating polarized proximal tubular epithelial cells expressing specific biomarkers known to be abundant along the in vivo human proximal tubule, including beta-catenin (red), occludin (green), aquaporin 1 (AQP1) (green), cilia (green), and Na/K-ATPase (pink), with scanning electron microscope (SEM) images showing cilia and a brush border, see lower right panel, labeled arrows.

FIG. 9A shows exemplary phase contract microscopic analysis of the proximal tubular epithelium (control-left panel: treated-right panel).

FIG. 9B shows exemplary Gentamicin-Induced Toxicity by LDH release (% control) that revealed significant cell damage after 10 mM of Gentamicin treatment for 48 hours. (*** $p<0.0.01$)

DEFINITIONS

Figure 1A:
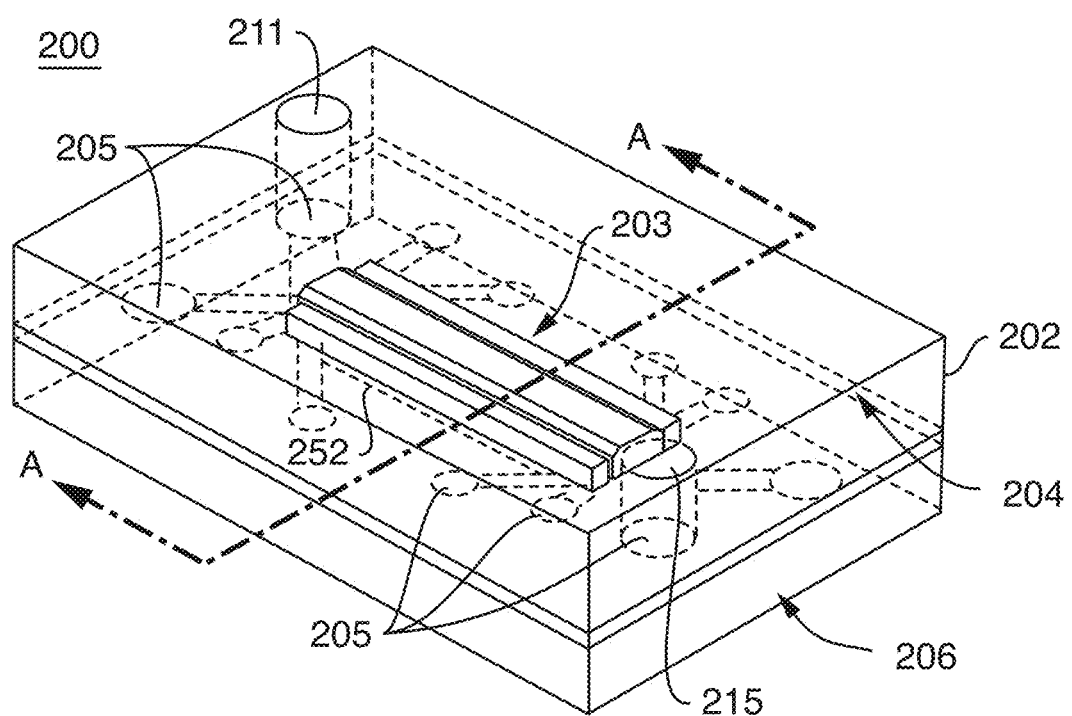
FIG. 1A illustrates one exemplary perspective view of a microfluidic device with microfluidic channels in accordance with an embodiment.

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

As used herein, the term "biopsy" refers to a sample of tissue that is removed from a body.

As used herein, the term "parenchymal cells" refer to functional cells of an organ in the body, such as ciliated epithelial cells and nonciliated epithelial cells, e.g. kidney cells, keratinocytes, hepatocytes, etc. This is in contrast to the stroma, which refers to the structural tissue of organs, e.g., connective tissues including but not limited to several cell types and extracellular products such as ECM, blood vessels, nerves, ducts, etc. Examples include but are not limited to: parenchyma of the kidney referring to epithelial tissue (including renal tubules and corpuscles) whereas blood vessels, nerves, and supporting connective tissue of the kidney comprise kidney stroma. The parenchyma of the brain is nervous tissue (nerve cells and glia cells). The blood vessels within the brain and the connective tissue associated with these blood vessels are referred to as stroma. The parenchyma of a malignant neoplasm comprises cancer cells. Other tissues, including blood vessels, which grow to support the tumor, are referred to as stroma.

As used herein, "Proximal Tubule-Chip" is interchangeable with "Proximal Tubule Kidney-Chip."

DESCRIPTION OF INVENTION

The present invention relates to microfluidic fluidic devices, methods and systems as microfluidic kidney on-chips, e.g. human Proximal Tubule-Chip.

In one embodiment, a human Proximal Tubule-Chip was developed, as described herein. In one embodiment, a human Proximal Tubule-Chip is contemplated for use in assessment of renal transporter-based drug-drug interactions. In one embodiment, a Proximal Tubule-Chip is an engineered microphysiological system where human proximal tubule cells and glomerular microvascular endothelial cells are co-cultured under (preferably continuous) medium flow and (optionally) mechanical forces (e.g. stretch).

Human primary proximal tubular epithelial cells were cultured in the proximal tubule channel on top of the porous membrane whereas glomerular microvascular endothelial cells were cultured on the opposite side of the same membrane in the vascular channel under continuous physiological flow to form a functional Proximal Tubule-Chip. This human Proximal Tubule-Chip recreates the natural tissue-tissue interface of the human kidney proximal tubule and the peritubular capillary. Thus a human Proximal Tubule-Chip may offer new ways to assess renal transporter-based drug-drug interactions and test for drug-associated kidney disorders.

I. Human Proximal Tubule-Chip.

Figure 3A:
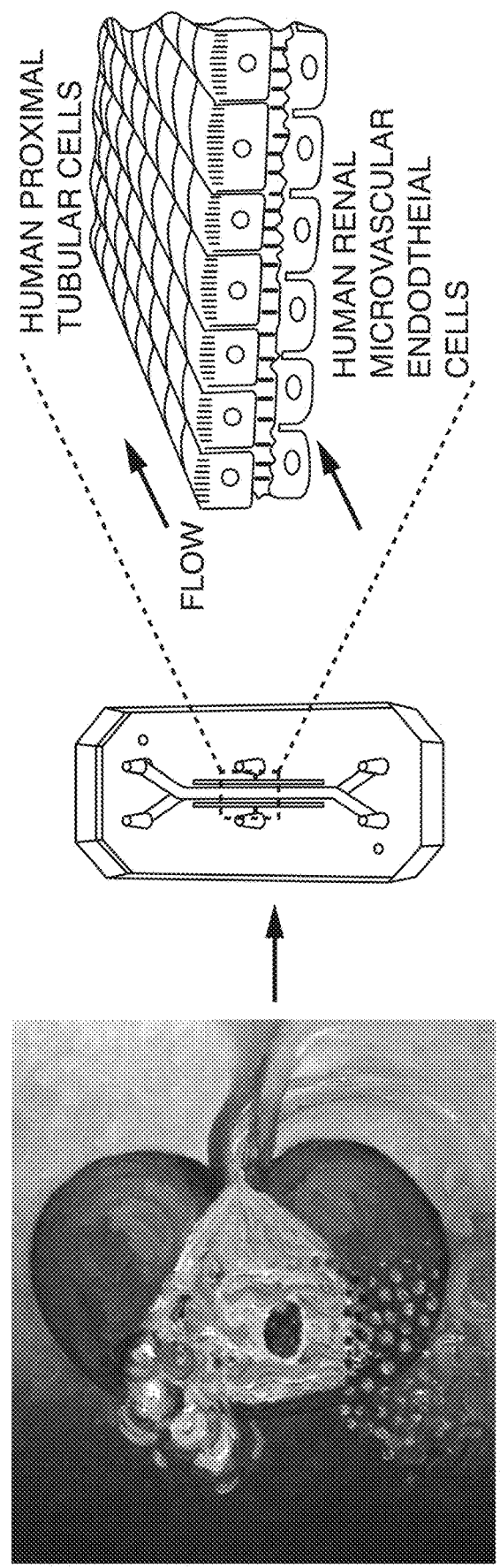
FIG. 3A shows one exemplary schematic of a human Proximal Tubule-Chip engineered using an S-1 Chip from Emulate, Inc., which is made of polydimethylsiloxane (PDMS) and contains an upper channel (1 mm high×1 mm wide) and a lower channel (0.2 mm high×1 mm wide), separated by a porous PDMS membrane that is coated with optimized extracellular matrix (ECM). The upper channel serves as a tubular lumen and is lined in one embodiment by primary human epithelial cells seeded on the ECM coated membrane. The lower channel, lined with endothelial cells, represents the peritubular vasculature.
Figure 3B:
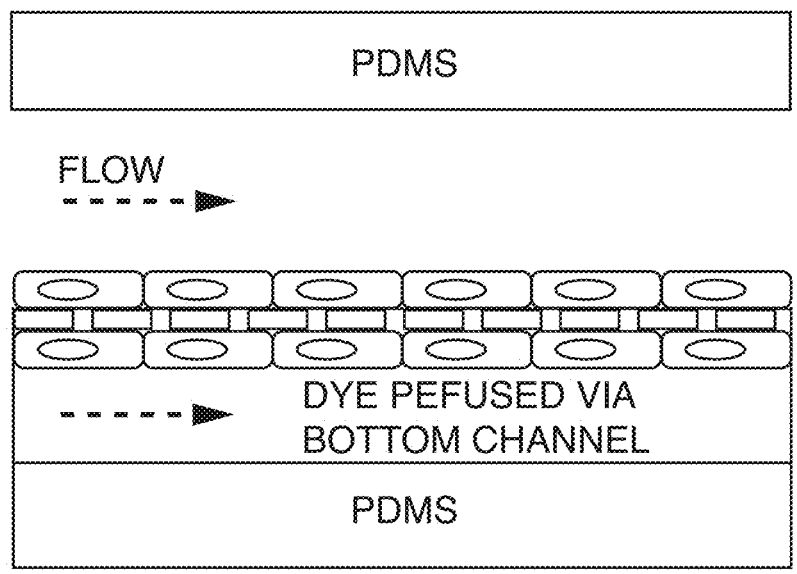
FIG. 3B shows an exemplary schematic of a fluidic chip. Polydimethylsiloxane (PDMS) (top of chip). Arrow shows directional fluid flow over the top of the parenchymal cells, e.g. kidney cells, attached to a membrane (dotted lines). Dye may be perfused through the fluid flowing through the bottom channel lined with endothelial cells over the bottom of the chip (PDMS).
Figure 3C:
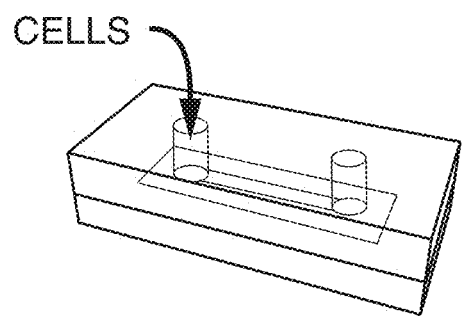
FIG. 3C shows one exemplary embodiment of a kidney-on-a-chip in which human kidney proximal tubular epithelial cells are cultured on the top of a porous membrane separating two channels, enabling analysis of transcellular transport, uptake and secretion (top-schematic). The upper fluorescence image of the epithelium shows enhanced formation of primary cilia (green) on the apical cell surfaces; the lower fluorescence cross-sectional view shows repolarization of Na+K+ ATPase (magenta) to the basal side.
Figure 3C:
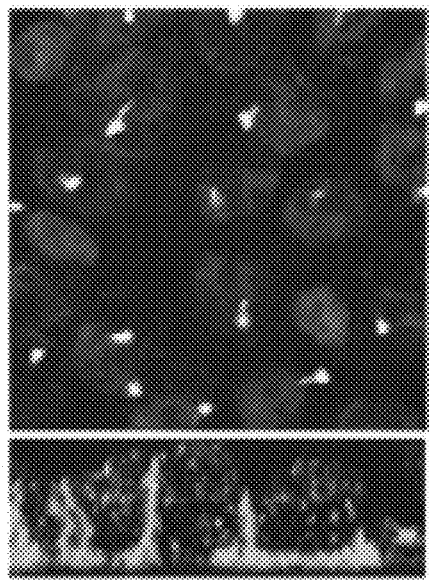

One embodiment of a human Proximal Tubule-Chip was engineered using the S-1 Chip from Emulate, Inc., See FIG. 3B.

FIG. 3A shows one exemplary schematic of a human Proximal Tubule-Chip engineered using an S-1 Chip from Emulate, Inc., which is made of polydimethylsiloxane (PDMS) and contains an upper channel (1 mm high×1 mm wide) and a lower channel (0.2 mm high×1 mm wide), separated by a porous PDMS membrane that is coated with optimized extracellular matrix (ECM). The upper channel serves as a tubular lumen and is lined in one embodiment by primary human epithelial cells seeded on the ECM coated membrane. In one embodiment, the lower channel, lined with endothelial cells, represents the peritubular vasculature.

FIG. 3B shows one exemplary embodiment of a kidney-on-a-chip in which human kidney proximal tubular epithelial cells are cultured on the top of a porous membrane separating two channels, enabling analysis of transcellular transport, uptake and secretion (top-schematic). The upper fluorescence image of the epithelium shows enhanced formation of primary cilia (green) on the apical cell surfaces; the lower fluorescence cross-sectional view shows repolarization of Na+K+ ATPase (magenta) to the basal side.

A. Proximal Tubule-Chip Has A Polarized Monolayer.

The Proximal Tubule-Chip formed polarized monolayer showing defined and orderly expression of the epithelial tight junction protein ZO-1 and the endothelial adherent protein VE-Cadherin. Polarized proximal tubular epithelial cells expressed specific makers known to be abundant along the proximal tubule, including beta-catenin, occludin, aquaporin 1 (AQP1), and Na/K-ATPase, and presented cilia and brush border. See, FIGS. 4A-B.

Figure 4A:
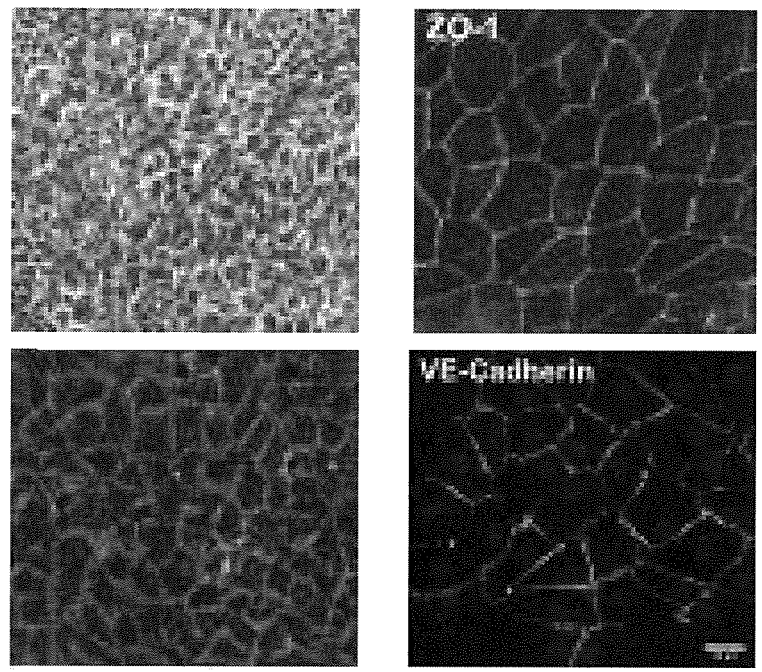
FIG. 4A-B shows exemplary microscopic images of cells within a human Proximal Tubule-Chip demonstrating a polarized epithelial monolayer: top channel (upper panels) and bottom channel (lower panels).
Figure 4B:
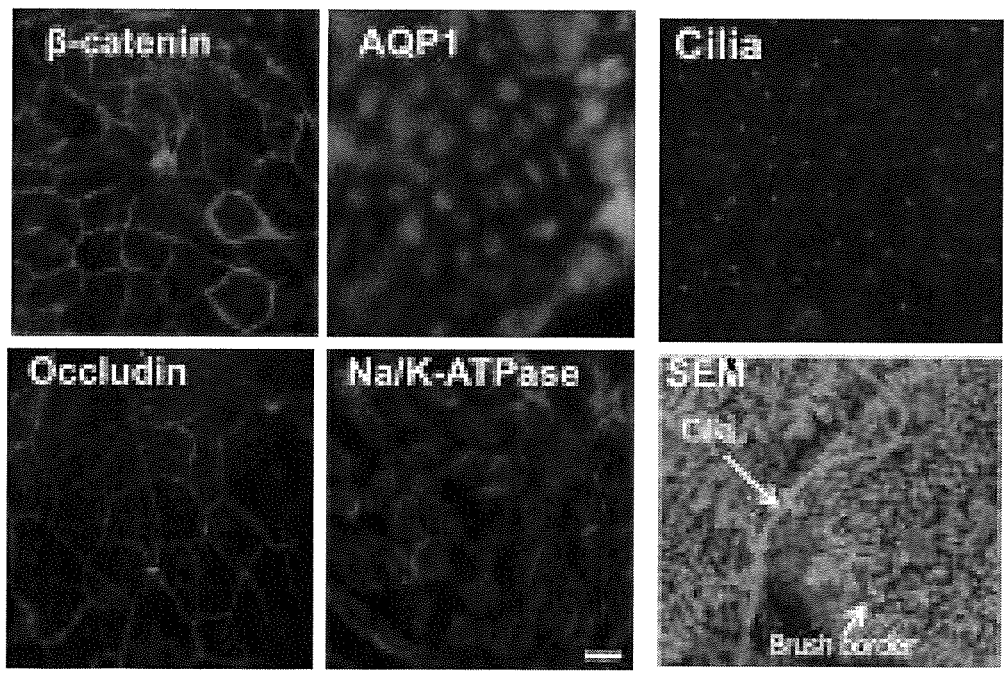

FIG. 4A-B shows exemplary microscopic images of cells within a human Proximal Tubule-Chip demonstrating a polarized epithelial monolayer: top channel (upper panels) and bottom channel (lower panels).

FIG. 4A shows exemplary microscopic images demonstrating a defined and orderly expression of the epithelial tight junction protein ZO-1 (upper right, green) and the endothelial adherent protein VE-Cadherin (lower right, green). Nuclei staining is colored blue.

FIG. 4B shows exemplary microscopic images of proximal tubule cells demonstrating polarized proximal tubular epithelial cells expressing specific biomarkers known to be abundant along the in vivo human proximal tubule, including beta-catenin (red), occludin (green), aquaporin 1 (AQP1) (green), cilia (green), and Na/K-ATPase (pink), with scanning electron microscope (SEM) images showing cilia and a brush border, see lower right panel, labeled arrows.

B. Functional Assessment of Transporter Molecules.

Relative gene expression of SGLT2, AQP1, and Na+/K+ ATPase was measured in control passage 1 (P1) proximal tubule cell populations compared to Proximal Tubule-Chip. Western blot analysis confirmed expression of uptake and efflux transporters such as P-glycoprotein (P-gp) and OCT2 (SLC22A2).

Figure 5A:
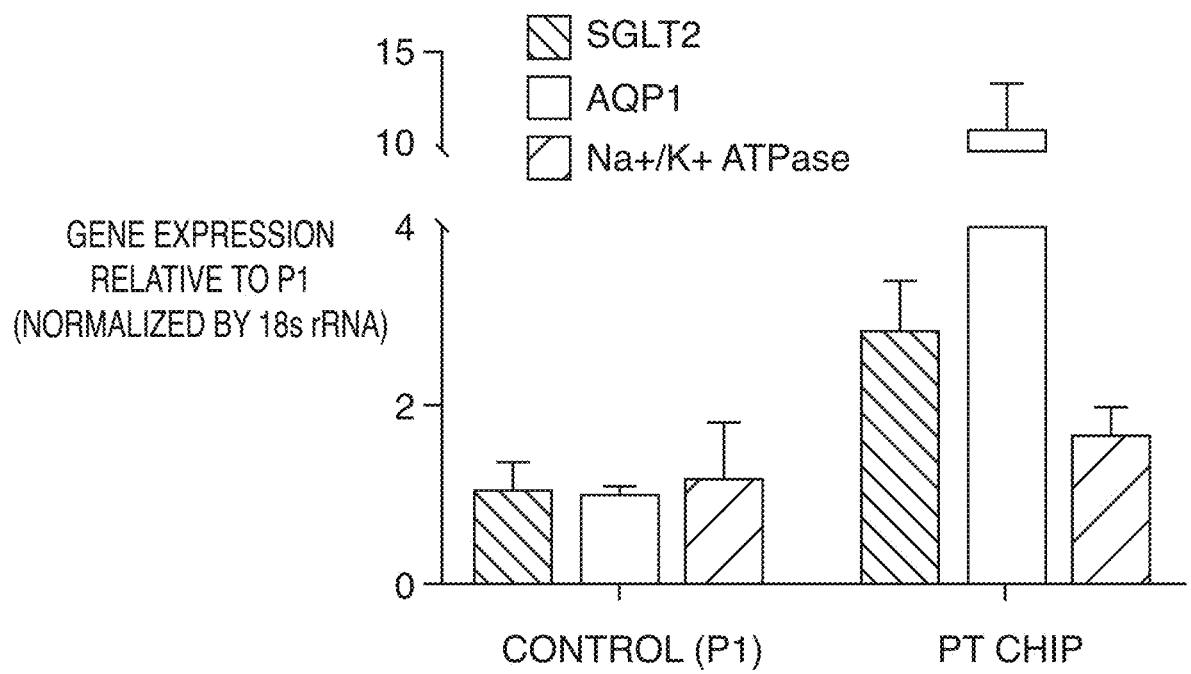
FIG. 5A-B shows exemplary relative gene expression (FIG. 5A) of SGLT2, AQP1, and Na+/K+ ATPase measured in control passage 1 (P1) proximal tubule cell vs Proximal Tubule-Chip. Western blot analysis (FIG. 5B) confirmed expression of uptake and efflux transporters such as P-glycoprotein (P-gp) and OCT2 (SLC22A2).
Figure 5B:
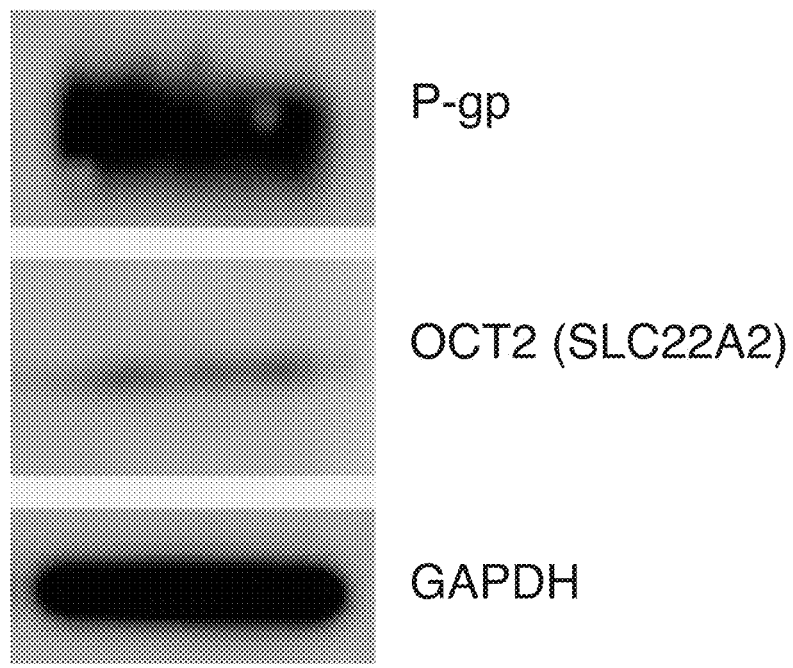

FIG. 5A-B shows exemplary relative gene expression (FIG. 5A) of SGLT2, AQP1, and Na+/K+ ATPase measured in control passage 1 (P1) proximal tubule cell vs Proximal Tubule-Chip. Western blot analysis (FIG. 5B) confirmed expression of uptake and efflux transporters such as P-glycoprotein (P-gp) and OCT2 (SLC22A2).

Transporter-mediated secretion of p-aminohippuric acid (PAH) and creatinine from the vascular channel to the luminal channel (basal to apical) was measured on Chip.

Figure 6A:
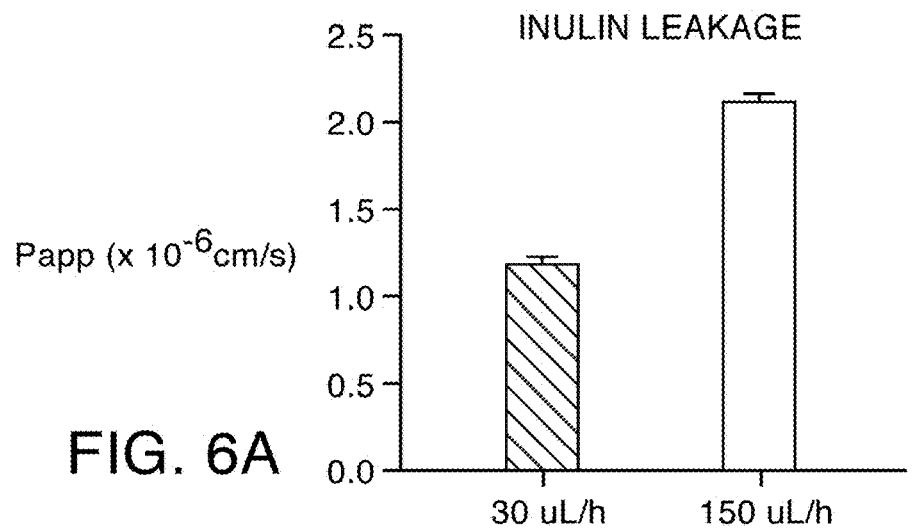
FIG. 6A shows that in one embodiment of a Proximal Tubule-Chip inulin permeability (leakage) was measured under two different flow rates, e.g. 30 ul/hr and 150 ul/hr.

FIG. 6A shows that in one embodiment of a Proximal Tubule-Chip inulin permeability (leakage) was measured under two different flow rates, e.g. 30 µl/hr and 150 µl/hr.

Figure 6B:
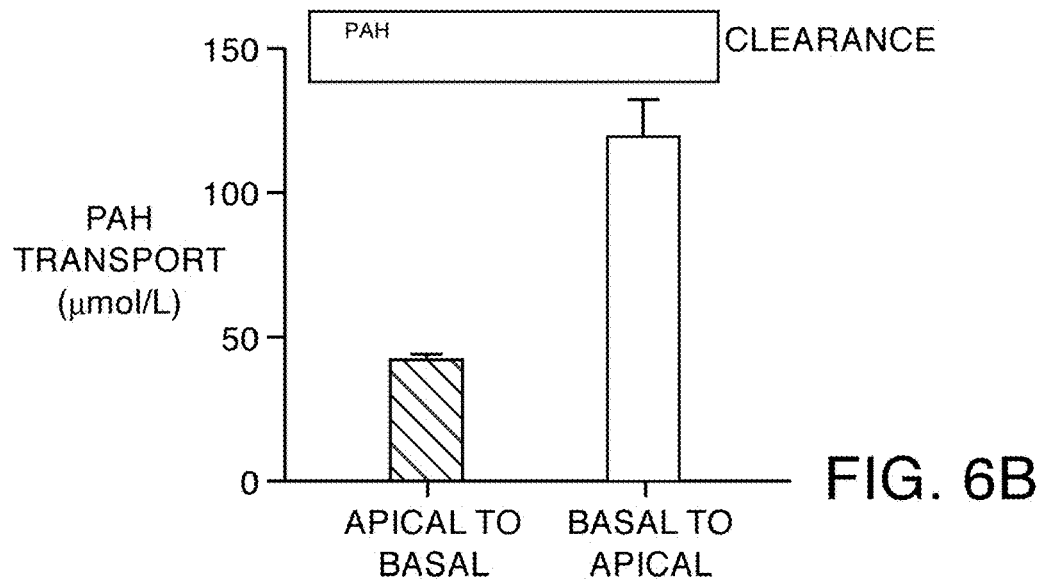
FIG. 6B and FIG. 6C shows that in one embodiment of a Proximal Tubule-Chip Transporter-mediated secretion of p-aminohippuric acid (PAH) and creatinine from the vascular channel to the luminal channel (basal to apical) was measured on Chip. As opposed to significantly less apical to basal transport.
Figure 6C:
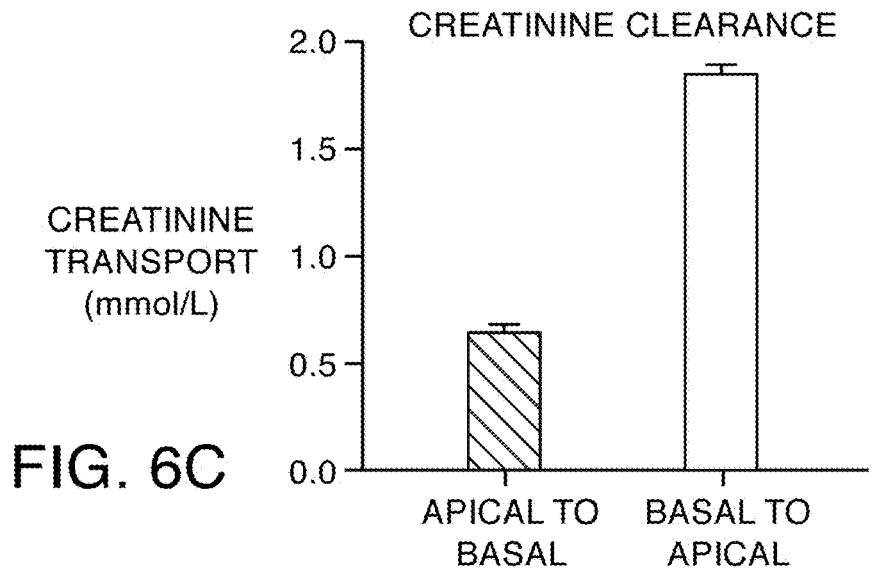

FIG. 6B and FIG. 6C shows that in one embodiment of a Proximal Tubule-Chip Transporter-mediated secretion of p-aminohippuric acid (PAH) and creatinine from the vascular channel to the luminal channel (basal to apical) was measured on Chip. As opposed to significantly less apical to basal transport.

Figure 7:
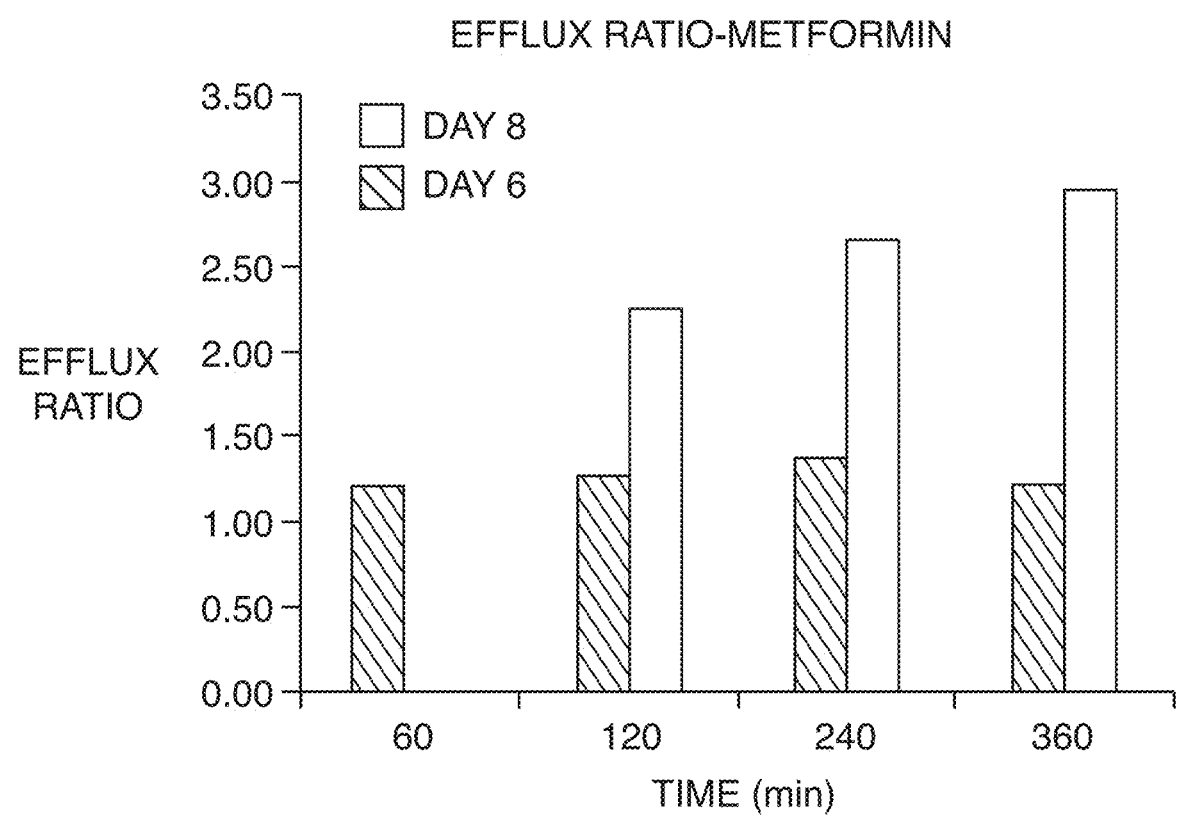
FIG. 7 shows that one embodiment of a Proximal Tubule-Chip, day 8, exhibited significant efflux of Metformin from the vascular channel to the luminal channel measured in a time-dependent manner as opposed to day 6 co-cultures. These results indicate that Metformin, creatinine, and PAH are actively transported by their respective proximal tubule transporters at 120, 240 and 260 minutes of incubation.

FIG. 7 shows that one embodiment of a Proximal Tubule-Chip, day 8, exhibited significant efflux of Metformin from the vascular channel to the luminal channel measured in a time-dependent manner as opposed to day 6 co-cultures. These results indicate that metformin, creatinine, and PAH are actively transported by their respective proximal tubule transporters at 120, 240 and 260 minutes of incubation.

These results suggest that metformin, creatinine, and PAH are actively transported by their respective proximal tubule transporters.

C. Megalin Protein Expression And Resorptive Capability of the Proximal Tubule Epithelium On-Chip.

One embodiment of a Proximal Tubule-Chip exhibited abundant megalin protein expression and resorptive capability of the proximal tubule epithelium by uptaking FITC-labeled human albumin. Megalin protein refers to Low density lipoprotein-related protein 2 also known as LRP2.

Figure 8:
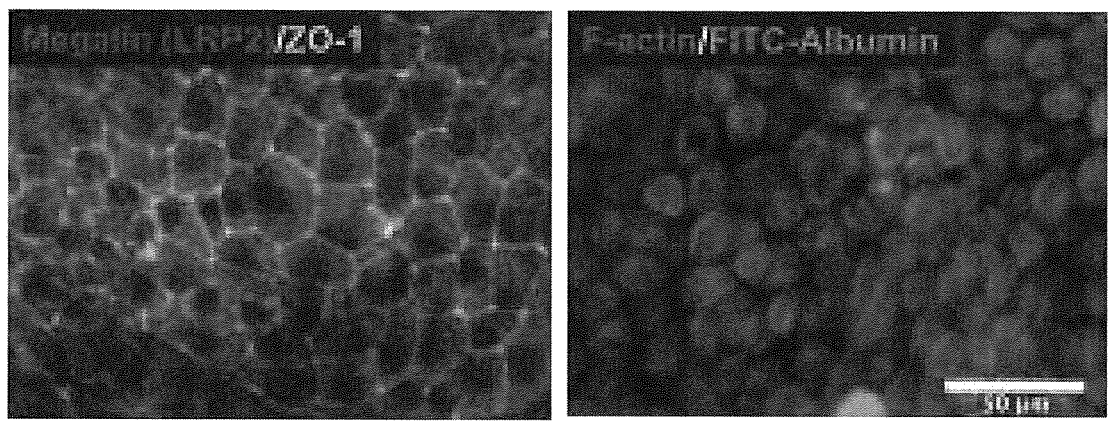
FIG. 8 shows that one embodiment of a Proximal Tubule-Chip exhibited abundant megalin protein expression (red) compared to ZO-1 (blue), left panel and resorptive capability of the proximal tubule epithelium by uptaking FITC-labeled human albumin (green), compared to F-actin staining (blue), right panel. Bar=50 µm.

FIG. 8 shows that one embodiment of a Proximal Tubule-Chip exhibited abundant megalin protein expression (red) compared to ZO-1 (blue), left panel and resorptive capability of the proximal tubule epithelium by uptaking FITC-labeled human albumin (green), compared to F-actin staining (blue), right panel. Bar=50 µm.

D. Gentamicin Induced Toxicity in Proximal Tubule-Chip.

Figure 9A:
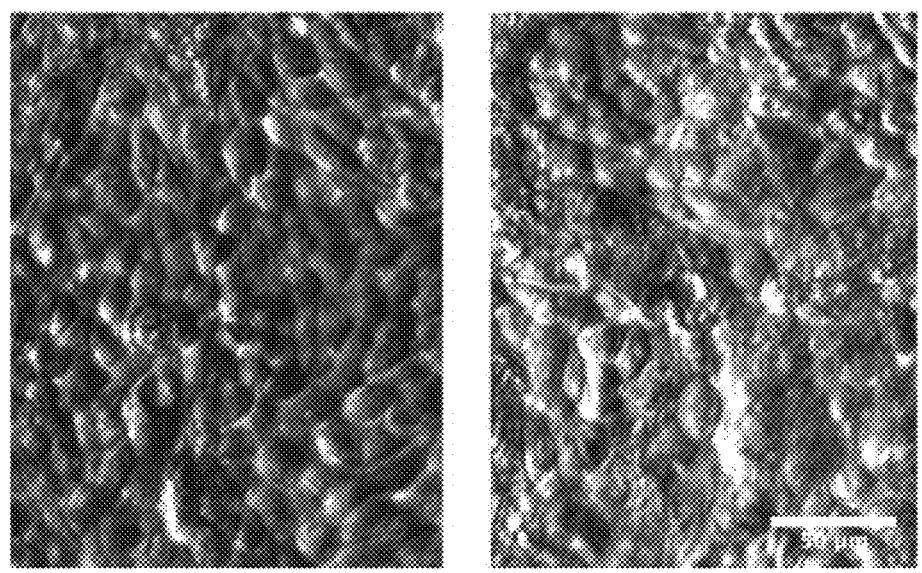
FIG. 9A-B shows that one embodiment of a Proximal Tubule-Chip exhibited Gentamicin Toxicity.
Figure 9B:
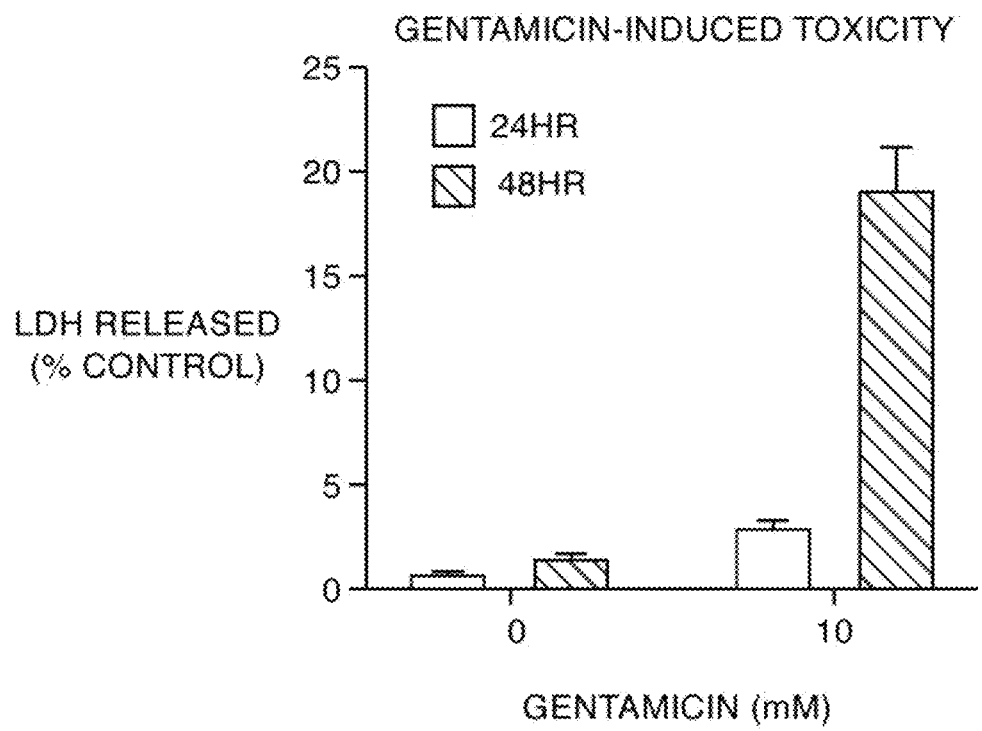

FIG. 9A-B shows that one embodiment of a Proximal Tubule-Chip exhibited Gentamicin Toxicity.

FIG. 9A shows exemplary phase contract microscopic analysis of the proximal tubular epithelium (control-left panel: treated-right panel).

FIG. 9B shows exemplary Gentamicin-Induced Toxicity by LDH release (% control) that revealed significant cell damage after 10 mM of Gentamicin treatment for 48 hours. (*** $p<0.0.01$).

In some embodiments, Proximal Tubule-Chips are evaluated for biomarkers of function and/or injury, e.g. Kidney Injury Marker 1 (KIM-1), etc.

In summary, we created a Proximal Tubule-Chip that recapitulates in vivo relevant tissue-tissue interface of the kidney proximal tubule. This kidney Proximal Tubule-Chip exhibited polarized epithelium and endothelium that reproduced baseline functions of the proximal tubule in vitro and demonstrated active transporters functions that are critical for normal kidney functions. These results suggest that the Proximal Tubule-Chip represents a physiologically relevant system for drug discovery and development applications.

Example A. Exemplary Kidney-Chip Protocol

Exemplary Materials are briefly described as follows.
ECM-Coating.
Sulfo-sanpah (Covachem, #13414), ER1 (0.5 mg/ml) in ER2 (50 mM HEPES buffer); Collagen IV (BD Corning, 50 µg/mL in Dulbecco's phosphate-buffered saline (DPBS); and Matrigel (BD Corning, reduced growth factor, 100 ug/ml DPBS).

Cells.
Top channel. Human Proximal Tubular Epithelial Cells (Lonza, RPTEC # CC-2553); and Bottom channel. Primary Human Glomerular microvascular Endothelial cells (Cell Systems. ACBRI 128), expand to P7 (e.g. passage 7).
Media.
Renal Epithelial Growth Medium (REGM™ Lonza, CC-3190) for Proximal tubule cells or REGM2 (from PromoCell, Cat # C-26130); and Kidney endothelial cell medium (Cell Systems, 4ZO-500).
Chip.
High shear chip; under flow shear; and Tall channel closed top-chip.
Experimental Reagents.
Collagen IV coated 6 well plate; and Corning BioCoat Collagen IV multiwall plates, Corning #354428.

One brief exemplary timeline is described as: Day −2: Chip coating; Day −1: Seeding endothelial cells; Day 0: Seeding proximal tubule epithelial cells; Day 0-7: Maintain chips; Day 7: Start Experiment (Study), e.g. 72 hours; and Day 10: End 72 hour Experiment (Study). Exemplary readouts include but are not limited to: Phase contrast microscopic images; immunofluorescent images; barrier function (in particular for kidney-chips, etc.); and Troponin I release (in particular for heart-chips, i.e. cardiac-chips).

A more detailed exemplary timeline, e.g. (proximal-tubule) Kidney-chip is described below.

Day 0: Chip Activation and Coating
1. Wash the top and bottom channels with 200 µl of 70% ethanol each channel.
2. Aspirate the fluid from both channels.
3. Wash both channels with 200 µl of sterile water each channel.
4. Aspirate the fluid from both channels.
5. Wash both channels with 200 µl of ER2 buffer each.
6. Add working solution of ER1 (0.5 mg/ml final concentration, 5 mg ER1/10 ml ER2) to top (50 ul) and bottom (20 µl) channels.
7. Activate the channel with UV light for 20 min.
8. Gently aspirate ER1 from the channels.
9. Wash both channels with 200 µl of ER2 each.
10. Wash both channels with 200 µl of PBS each.
11. Aspirate PBS from both channels gently.
12. Add ECM in PBS (Collagen IV (50 µg/ml)+Matrigel (100 ug/ml)) to top (50 µl) and bottom (20 µl) channels of a standard S-1 closed top chip. In one contempalted embodiment, a high shear chip may be used with 15 µl each for top and bottom channels.
13. Incubate the chip at 37° C. overnight.

Next day, gently wash the channel with endothelial media.
Day 1: Endothelial Cell Seeding
1. Expand kidney Glomerular endothelial cells for 2-3 days.
    Add 5 ml of attachment factor to T75 flask and leave at least 5 seconds.
    Aspirate the attachment factor and add 20-30 ml of fresh growth media to flask and incubate at 37° C. until media is at 37° C.
    Thaw a frozen vial of cells at 37° C. in a water bath and immediately transfer the cells into a conical tube containing 14 ml of cold growth media.
    Centrifuge the cells at 900×g for 10 min at 4° C.
    Gently aspirate the supernatant.
    Resuspend the cells in 2 ml growth media and add the cells into T-75 flask.
    Culture the cells at 37° C. for 2-3 days.

2. On day of cell seeding, trypsinize the cells and spin at 900×g for 10 min at 4° C.
3. Count the cells and make 5×10$^6$ cells/ml density for a tall channel chip and seed 20 μl for bottom channel. For a high shear chip, dilute cells at 10×10$^6$ cells/ml then add 10 ul of cells into bottom channel. Final cell concentration is 100,000 cells/chip.
4. Flip the chip and incubate for 90 minutes (min) at 37° C. in an incubator.
5. Add media on top of the inlet and outlet port, gravity washing and feeding.
6. Incubate for 1 day.
7. Prior to proximal cell seeding, stop flow using tips for bottom channel.

Day 2: Proximal Tubular Cell Seeding
1. Expand Human Primary Proximal Tubular cells in 6-well plate (Collagen IV coated) for 3-4 days.
   Coat 6 well plates with Collagen IV (50 μg/ml)/Matrigel (100 μg/ml) for at least 2 hours (h) at 37° C., or use a Col IV coated plate (e.g. Corning #354428).
   Wash with Dulbecco's phosphate-buffered saline (DPBS) and seed Renal Proximal tubular cells at 180,000 cells per well (20,000 cells/cm$^2$).
   Culture for 3-4 days.
2. Trypsinize the cells and count
3. Dilute 2×10$^6$ cells/ml in media for a tall channel chip and seed 40 μl into top channel. For high shear chip, make 8×10$^6$ cells/ml density and seed 10 μl of cells into top channel. Final cell concentration is 80,000 cells per chip.
4. Incubate for 90 min at 37° C. incubator.
5. Add media REGM on top of the inlet and outlet port, gravity washing and feeding using tips.
6. Incubate for 1-2 days static (i.e. no flow).

Day 4: Start Flow at 30 ul/hr.
1. Warm media degassing using steriflip for 15 min at 37° C. bead bath.
2. Incubate the media at 37° C. in an incubator after loosening the cap, i.e. unscrewing the cap a bit, but not enough to allow contamination of the media, to ensure gas equilibration.
3. Add 3 ml media in Inlet port and 0.3 ml in Outlet port Reservoir.
4. Prime the perfusion manifold in the culture module.
5. Connect the chip to the perfusion manifold and start flow.
6. Change media every other day.
7. Culture for 6-7 days.

Day 7-10: Nephrotoxin testing and readouts.
Outflow from chips, (e.g. S1—closed top chip; and high shear (HS) chip) was collected for certain readouts. For reference, kidney endothelial media contains 5% FBS while the kidney epithelial media contains 0.5% FBS (fetal bovine serum).

Read outs include but are not limited to: a Kidney injury panel from MSD (K15189D, K15188D); Kidney gene expression: transporters (MRP2, 4, MDR1, MATE1/2-K, OAT1, OAT2, OAT3, OATP4C. OCT2, MRP1/3/5/6, etc.); Immunostaining: antibodies (MRP2, 4, MDR1, MATE1/2-K, OAT1, OAT2, OAT3, OATP4C, OCT2, MRP1/3/5/6, etc.).

DETAILED DESCRIPTION OF INVENTION

The present invention relates to microfluidic fluidic devices, methods and systems as microfluidic kidney on-chips, e.g. human Proximal Tubule-Chip.

Embodiments include methods for seeding microfluidic chips with a sample, such as seeding kidney cells obtained from one source, in numerous duplicate closed or open top chips, then challenging the chosen chip with a test compound, e.g. by contacting with an agent; drug, infection with a pathogen, i.e. bacterial, viral, fungal; etc., Such contacting may be by using either a single concentration or one specific dilution or a dilution series tested on a group of duplicate chips under flow during incubation, either during or after contacting. In some embodiments, a blood sample would be flowed over contacted cells in said chip. In some embodiments, a white blood cell sample would be flowed over contacted cells in said chip.

After which, effluent fluid would be sampled at certain time points for collecting samples, in some embodiments. In some embodiments, blood cells from a blood sample flowed through the chip would be collected for analysis. In other embodiments, cells would be lysed within the microchannel then flushed into the effluent tubing for collection for further processing, such as for RNA isolation by cesium chloride centrifugation, etc.

Isolated sample material would then be used to assess a profile of one or more cell type involved in the chip, including but not limited to cells located within the chip, cells attached to the chip, cells flowing through the chip, e.g. blood cells, compounds released by cells that were flowed over or in contact with treated cells.

As nonlimiting examples, test agents may include chemicals, such as pesticides, herbicides, fungicides, pathogens, toxins, in the environment, etc.

I. Microfluidic Chips, Devices and Systems.

Microfluidic chips, devices, and systems contemplated for use include but are not limited to chips described in Bhatia and Ingber, "Microfluidic organs-on-chips." Nature Biotechnology, 32(8):760-722, 2014; and related patent applications; and further include a wide range of chips of which some are briefly described in Zhang and Radisic, "Organ-on-a-chip devices advance to market." Lab On A Chip, (2017), for some examples, herein incorporated by reference in its entirety. The following section is merely for providing nonlimiting examples of embodiments that may find use as microfluidic devices. Moreover, exemplary embodiments of ECM, gels, etc., may find use with any microfluidic device used for microfluidic kidney-chips. It is not meant to limit the type of cells added to organ-chips, including but not limited to white blood cells, immune cells, etc.

It is not meant to limit the type of treatment of a fluidic kidney-chip, including but not limited to inflammatory induction, such as TNFalpha treatment, inflammaotry mediator treatment, etc. Thus, in some embodiments, fluidic kidney-chip as described herein are contemplated for use for decoupling cell populations, e.g. analyzing separate cell samples from the same chip.

In some embodiments, readouts measure the effect of inflammatory cytokines on organ-chips as described herein, for one example, to measure the effect upon fluidic kidney-chip barrier function and cytokine release. In some embodiments, readouts are from assays, such as barrier function, including particle diffusion, transepithelial electric resistance (TEER), apparent permeability, immunohistochemistry, etc.

More specifically, one embodiment of a kidney Proximal Tubule-Chip, e.g. one embodiment of a kidney-on-a-chip is contemplated for use in which human kidney proximal tubular epithelial cells are cultured on top of a porous membrane separating two channels, enabling analysis of transcellular transport, uptake and secretion. In some embodiments, a kidney-chip comprises of the human kidney cultured on top of a porous membrane separating two channels. Parenchyma refers to epithelial tissue (including renal tubules and corpuscles) whereas blood vessels, nerves, and supporting connective tissue of the kidney comprise kidney stroma.

II. Closed Top Chips.

The present disclosure relates to fluidic kidney-chip, such as fluidic devices comprising one or more cells types for the simulation one or more of the function of kidney glomerular components, nephrons, etc. Accordingly, the present disclosure additionally describes closed-top kidney-chips, see, e.g. schematic in FIG. 1A-B. In some embodiments, a fluidic kidney chip is a closed top device.

Figure 1B:
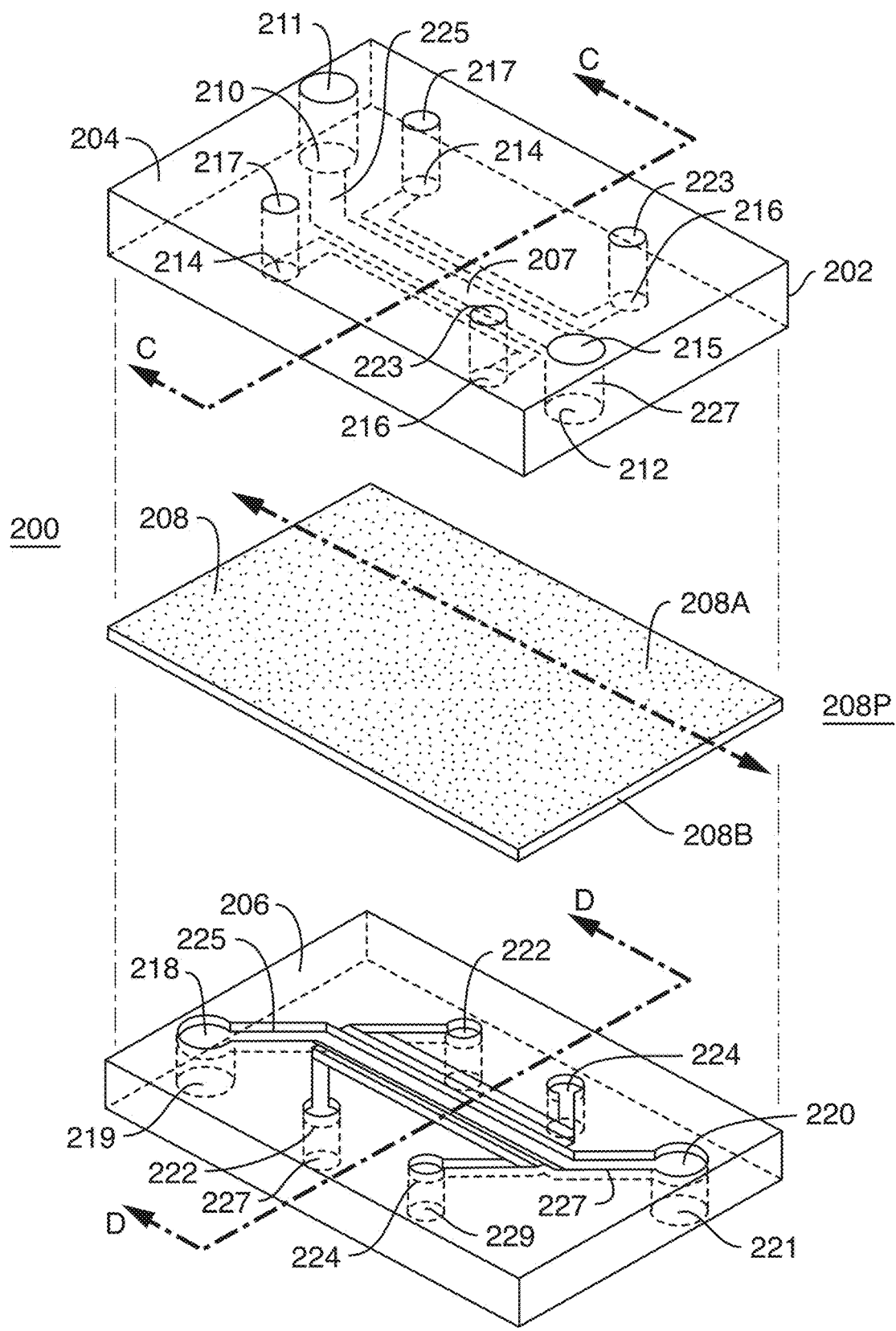
FIG. 1B illustrates one exemplary exploded view of the device in accordance with an embodiment, showing a microfluidic channel in a top piece and a microfluidic channel in a bottom piece, separated by a membrane.

FIG. 1A-1B illustrates a perspective view of the devices in accordance with some embodiments described herein. For example, as shown in FIGS. 1A-1B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is only exemplary and not limited to the configuration shown in FIG. 1A-1B. While operating chambers 252 (e.g., as a pneumatics means to actuate the membrane 208, see the International Appl. No. PCT/US2009/050830 for further details of the operating chambers, the content of which is incorporated herein by reference in its entirety) are shown in FIGS. 1A-1B, they are not required in all of the embodiments described herein. In some embodiments, the devices do not comprise operating chambers on either side of the first chamber and the second chamber. For example, FIG. 1B shows a device that does not have an operating channel on either side of the first chamber and the second chamber. In other embodiments, the devices described herein can be configured to provide other means to actuate the membrane, e.g., as described in the International Pat. Appl. No. PCT/US2014/071570, the content of which is incorporated herein by reference in its entirety.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are incorporated herein by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof. As used herein, the term "rigid" refers to a material that is stiff and does not bend easily, or maintains very close to its original form after pressure has been applied to it. The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof. As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally or alternatively, at least a portion of the first structure 204 and/or second structure 206 can be made of non-flexible or rigid materials like glass, silicon, hard plastic, metal, or any combinations thereof.

The membrane 208 can be made of the same material as the first structure 204 and/or second structure 206 or a material that is different from the first structure 204 and/or second structure 206 of the devices described herein. In some embodiments, the membrane 208 can be made of a rigid material. In some embodiments, the membrane is a thermoplastic rigid material. Examples of rigid materials that can be used for fabrication of the membrane include, but are not limited to, polyester, polycarbonate or a combination thereof. In some embodiments, the membrane 208 can comprise a flexible material, e.g., but not limited to PDMS. Additional information about the membrane is further described below.

In some embodiments, the first structure and/or second structure of the device and/or the membrane can comprise or is composed of an extracellular matrix polymer, gel, and/or scaffold. Any extracellular matrix can be used herein, including, but not limited to, silk, chitosan, elastin, collagen, proteoglycans, hyaluronic acid, collagen, fibrin, and any combinations thereof.

The device in FIG. 1A can comprise a plurality of access ports 205. In addition, the branched configuration 203 can comprise a tissue-tissue interface simulation region (membrane 208 in FIG. 1B) where cell behavior and/or passage of gases, chemicals, molecules, particulates and cells are monitored. FIG. 1B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204, 206 when the portions 204, 206 are mounted to one another to form the overall body.

The first outer body portion or first structure 204 can have a thickness of any dimension, depending, in part, on the height of the first chamber 204. In some embodiments, the thickness of the first outer body portion or first structure 204 can be about 1 mm to about 100 mm, or about 2 mm to about 75 mm, or about 3 mm to about 50 mm, or about 3 mm to about 25 mm. In some embodiments, the first outer body portion or first structure 204 can have a thickness that is more than the height of the first chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the first outer body portion or first structure 204 as thin as possible such that cells on the membrane can be visualized or detected by microscopic, spectroscopic, and/or electrical sensing methods.

The second outer body portion or second structure 206 can have a thickness of any dimension, depending, in part, on the height of the second chamber 206. In some embodiments, the thickness of the second outer body portion or second structure 206 can be about 50 µm to about 10 mm, or about 75 µm to about 8 mm, or about 100 µm to about 5 mm, or about 200 µm to about 2.5 mm. In one embodiment, the thickness of the second outer body portion or second structure 206 can be about 1 mm to about 1.5 mm. In one embodiment, the thickness of the second outer body portion or second structure 206 can be about 0.2 mm to about 0.5 mm. In some embodiments, the second outer first structure and/or second structure portion 206 can have a thickness that is more than the height of the second chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the second outer body portion or second structure 206 as thin as possible such that cells on the membrane can be visualized or detected by microscopic, spectroscopic, and/or electrical sensing methods.

In some embodiments, the first chamber and the second chamber can each independently comprise a channel. The channel(s) can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 1B illustrates an exploded view of the device in accordance with an embodiment. As shown in FIG. 1B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 1B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

The device 200 can also comprise an outlet channel 227 connecting an outlet fluid port 212 to the first chamber 204. The outlet channels and outlet ports can also be used to introduce cells, agents (e.g., but not limited to, stimulants, drug candidate, particulates), airflow, and/or cell culture media into the first chamber 204.

Although the inlet and outlet apertures 211, 215 are shown on the top surface of the first structure 204 and are located perpendicular to the inlet and outlet channels 225, 227, one or more of the apertures 211, 215 can be located on one or more lateral surfaces of the first structure and/or second structure such that at least one of the inlet and outlet apertures 211, 215 can be in-plane with the inlet and/or outlet channels 225, 227, respectively, and/or be oriented at an angle from the plane of the inlet and/or outlet channels 225, 227.

In another embodiment, the fluid passing between the inlet and outlet fluid ports can be shared between the first chamber 204 and second chamber 206. In either embodiment, characteristics of the fluid flow, such as flow rate, fluid type and/or composition, and the like, passing through the first chamber 204 can be controllable independently of fluid flow characteristics through the second chamber 206 and vice versa.

In some embodiments, while not necessary, the first structure 204 can include one or more pressure inlet ports 214 and one or more pressure outlet ports 216 in which the inlet ports 214 are in communication with corresponding apertures 217 located on the outer surface of the device 200. Although the inlet and outlet apertures are shown on the top surface of the first structure 204, one or more of the apertures can alternatively be located on one or more lateral sides of the first structure and/or second structure. In operation, one or more pressure tubes (not shown) connected to an external force source (e.g., pressure source) can provide positive or negative pressure to the device via the apertures 217. Additionally, pressure tubes (not shown) can be connected to the device 200 to remove the pressurized fluid from the outlet port 216 via the apertures 223. It should be noted that the device 200 can be set up such that the pressure port 214 is an outlet and pressure port 216 is an inlet. It should be noted that although the pressure apertures 217, 223 are shown on the top surface of the first structure 204, one or more of the pressure apertures 217, 223 can be located on one or more side surfaces of the first structure 204.

Referring to FIG. 1B, in some embodiments, the second structure 206 can include one or more inlet fluid ports 218 and one or more outlet fluid ports 220. As shown in FIG. 1B, the inlet fluid port 218 is in communication with aperture 219 and outlet fluid port 220 is in communication with aperture 221, whereby the apertures 219 and 221 are located on the outer surface of the second structure 206. Although the inlet and outlet apertures are shown on the surface of the second structure, one or more of the apertures can be alternatively located on one or more lateral sides of the second structure.

As with the first outer body portion or first structure 204 described above, one or more fluid tubes connected to a fluid source can be coupled to the aperture 219 to provide fluid to the device 200 via port 218. Additionally, fluid can exit the device 200 via the outlet port 220 and outlet aperture 221 to a fluid reservoir/collector or other component. It should be noted that the device 200 can be set up such that the fluid port 218 is an outlet and fluid port 220 is an inlet.

In some embodiments, the second outer body portion and/or second structure 206 can include one or more pressure inlet ports 222 and one or more pressure outlet ports 224. In some embodiments, the pressure inlet ports 222 can be in communication with apertures 227 and pressure outlet ports 224 are in communication with apertures 229, whereby apertures 227 and 229 are located on the outer surface of the second structure 206. Although the inlet and outlet apertures are shown on the bottom surface of the second structure 206, one or more of the apertures can be alternatively located on one or more lateral sides of the second structure. Pressure tubes connected to an external force source (e.g., pressure source) can be engaged with ports 222 and 224 via corresponding apertures 227 and 229. It should be noted that the device 200 can be set up such that the pressure port 222 is an outlet and fluid port 224 is an inlet.

In some embodiments where the operating channels (e.g., 252 shown in FIG. 1A) are not mandatory, the first structure 204 does not require any pressure inlet port 214, pressure outlet port 216. Similarly, the second structure 206 does not require any pressure inlet port 222 or pressure outlet port 224.

In an embodiment, the membrane 208 is mounted between the first structure 204 and the second structure 206, whereby the membrane 208 is located within the first structure 204 and/or second structure 206 of the device 200 (see, e.g., FIG. 1B). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, the membrane 208 in one embodiment can be made of a material which allows the membrane 208 to undergo stress and/or strain in response to an external force (e.g., cyclic stretching or pressure). In one embodiment, the membrane 208 can be made of a material which allows the membrane 208 to undergo stress and/or strain in response to pressure differentials present between the first chamber 204, the second chamber 206 and the operating channels 252. Alternatively, the membrane 208 is relatively inelastic or rigid in which the membrane 208 undergoes minimal or no movement.

In some embodiments where the device simulates a function of a proximal-tubule tissue, the membrane can be rigid.

The first chamber 204 and/or the second chamber 206 can have a length suited to the need of an application (e.g., a physiological system to be modeled), desirable size of the device, and/or desirable size of the view of field. In some embodiments, the first chamber 204 and/or the second chamber 206 can have a length of about 0.5 cm to about 10 cm. In one embodiment, the first chamber 204 and/or the second chamber 206 can have a length of about 1 cm to about 3 cm. In one embodiment, the first chamber 204 and/or the second chamber 206 can have a length of about 2 cm.

The width of the first chamber and/or the second chamber can vary with desired cell growth surface area. The first chamber 204 and the second chamber 206 can each have a range of width dimension (shown as W in FIG. 1B) between 100 microns and 50 mm, or between 200 microns and 10 mm, or between 200 microns and 1500 microns, or between 400 microns and 1 mm, or between 50 microns and 2 mm, or between 100 microns and 5 mm. In some embodiments, the first chamber 204 and the second chamber 206 can each have a width of about 500 microns to about 2 mm. In some embodiments, the first chamber 204 and the second chamber 206 can each have a width of about 1 mm.

In some embodiments, the widths of the first chamber and the second chamber can be configured to be different, with the centers of the chambers aligned or not aligned. In some embodiments, the channel heights, widths, and/or cross sections can vary along the length of the devices described herein.

The heights of the first chamber and the second chamber can vary to suit the needs of desired applications (e.g., to provide a low shear stress, and/or to accommodate cell size). The first chamber and the second chamber of the devices described herein can have the same heights or different heights. In some embodiments, the height of the second chamber 206 can be substantially the same as the height of the first chamber 204.

In some embodiments, the height of at least a length portion of the first chamber 204 (e.g., the length portion where the cells are designated to grow) can be substantially greater than the height of the second chamber 206 within the same length portion. For example, the height ratio of the first chamber to the second chamber can be greater than 1:1, including, for example, greater than 1.1:1, 1.5:1, 2:1, 2.5:1, 3:1, 3.5:1, 4:1, 4.5:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1. In some embodiments, the height ratio of the first chamber to the second chamber can range from 1.1:1 to about 50:1, or from about 2.5:1 to about 50:1, or from 2.5 to about 25:1, or from about 2.5:1 to about 15:1. In one embodiment, the height ratio of the first chamber to the second chamber ranges from about 1:1 to about 20:1. In one embodiment, the height ratio of the first chamber to the second chamber ranges from about 1:1 to about 15:1. In one embodiment, the height ratio of the first chamber to the second chamber can be about 10:1.

The height of the first chamber 204 can be of any dimension, e.g., sufficient to accommodate cell height and/or to permit a low shear flow. For example, in some embodiments, the height of the first chamber can range from about 100 μm to about 50 mm, about 200 μm to about 10 mm, about 500 μm to about 5 mm, or about 750 um to about 2 mm. In one embodiment, the height of the first chamber can be about 150 um. In one embodiment, the height of the first chamber can be about 1 mm.

The height of the second chamber 206 can be of any dimension provided that the flow rate and/or shear stress of a medium flowing in the second chamber can be maintained within a physiological range, or does not cause any adverse effect to the cells. In some embodiments, the height of the second chamber can range from 20 μm to about 1 mm, or about 50 μm to about 500 μm, or about 75 μm to about 400 μm, or about 100 μm to about 300 μm. In one embodiment, the height of the second chamber can be about 150 In one embodiment, the height of the second chamber can be about 100 μm.

The first chamber and/or the second chamber can have a uniform height along the length of the first chamber and/or the second chamber, respectively. Alternatively, the first chamber and/or the second chamber can each independently have a varying height along the length of the first chamber and/or the second chamber, respectively. For example, a length portion of the first chamber can be substantially taller than the same length portion of the second chamber, while the rest of the first chamber can have a height comparable to or even smaller than the height of the second chamber.

In some embodiments, the first structure and/or second structure of the devices described herein can be further adapted to provide mechanical modulation of the membrane. Mechanical modulation of the membrane can include any movement of the membrane that is parallel to and/or perpendicular to the force/pressure applied to the membrane, including, but are not limited to, stretching, bending, compressing, vibrating, contracting, waving, or any combinations thereof. Different designs and/or approaches to provide mechanical modulation of the membrane between two chambers have been described, e.g., in the International Patent App. Nos. PCT/US2009/050830, and PCT/US2014/071570, the contents of which are incorporated herein by reference in their entireties, and can be adapted herein to modulate the membrane in the devices described herein.

In some embodiments, the devices described herein can be placed in or secured to a cartridge. In accordance with some embodiments of some aspects described herein, the device can be integrated into a cartridge and form a monolithic part. Some examples of a cartridge are described in the International Patent App. No. PCT/US2014/047694, the content of which is incorporated herein by reference in its entirety. The cartridge can be placed into and removed from a cartridge holder that can establish fluidic connections upon or after placement and optionally seal the fluidic connections upon removal. In some embodiments, the cartridge can be incorporated or integrated with at least one sensor, which can be placed in direct or indirect contact with a fluid flowing through a specific portion of the cartridge during operation. In some embodiments, the cartridge can be incorporated or integrated with at least one electric or electronic circuit, for example, in the form of a printed circuit board or flexible circuit. In accordance with some embodiments of some aspects described herein, the cartridge can comprise a gasketing embossment to provide fluidic routing.

In some embodiments, the cartridge and/or the device described herein can comprise a barcode. The barcode can be unique to types and/or status of the cells present on the membrane. Thus, the barcode can be used as an identifier of each device adapted to mimic function of at least a portion of a specific tissue and/or a specific tissue-specific condition. Prior to operation, the barcode of the cartridge can be read by an instrument so that the cartridge can be placed and/or aligned in a cartridge holder for proper fluidic connections and/or proper association of the data obtained during operation of each device. In some embodiments, data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

In some embodiments, the device can be connected to the cartridge by an interconnect adapter that connects some or all of the inlet and outlet ports of the device to microfluidic channels or ports on the cartridge. Some examples interconnect adapters are disclosed in U.S. Provisional Application No. 61/839,702, filed on Jun. 26, 2013, and the International Patent Application No. PCT/US2014/044417 filed Jun. 26, 2014, the contents of each of which are hereby incorporated by reference in their entirety. The interconnect adapter can include one or more nozzles having fluidic channels that can be received by ports of the device described herein. The interconnect adapter can also include nozzles having fluidic channels that can be received by ports of the cartridge.

In some embodiments, the interconnect adaptor can comprise a septum interconnector that can permit the ports of the device to establish transient fluidic connection during operation, and provide a sealing of the fluidic connections when not in use, thus minimizing contamination of the cells and the device. Some examples of a septum interconnector are described in U.S. Provisional Application No. 61/810,944 filed Apr. 11, 2013, the content of which is incorporated herein by reference in its entirety.

Membrane: The membrane 208 is oriented along a plane 208P parallel to the x-y plane between the first chamber 204 and the second chamber 206 as shown in FIG. 1B. It should be noted that although one membrane 208 is shown in FIG. 1B, more than one membrane 208 can be configured in devices which comprise more than two chambers. The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through. In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In some embodiments, a selectively-permeable membrane can allow certain cell types to pass therethrough but not other cell types.

The permeability of the membrane to individual matter/species can be determined based on a number of factors, including, e.g., material property of the membrane (e.g., pore size, and/or porosity), interaction and/or affinity between the membrane material and individual species/matter, individual species size, concentration gradient of individual species between both sides of the membrane, elasticity of individual species, and/or any combinations thereof. A porous membrane can have through-holes or pore apertures extending vertically and/or laterally between two surfaces 208A and 208B of the membrane (FIG. 1B), and/or a connected network of pores or void spaces (which can, for example, be openings, interstitial spaces or hollow conduits) throughout its volume. The porous nature of the membrane can be contributed by an inherent physical property of the selected membrane material, and/or introduction of conduits, apertures and/or holes into the membrane material.

In some embodiments, a membrane can be a porous scaffold or a mesh. In some embodiments, the porous scaffold or mesh can be made from at least one extracellular matrix polymer (e.g., but not limited to collagen, alginate, gelatin, fibrin, laminin, hydroxyapatite, hyaluronic acid, fibroin, and/or chitosan), and/or a biopolymer or biocompatible material (e.g., but not limited to, polydimethylsiloxane (PDMS), polyurethane, styrene-ethylene-butylene-styrene (SEBS), poly(hydroxyethylmethacrylate) (pHEMA), polyethylene glycol, polyvinyl alcohol and/or any biocompatible material described herein for fabrication of the device first structure and/or second structure) by any methods known in the art, including, e.g., but not limited to, electrospinning, cryogelation, evaporative casting, and/or 3D printing. See, e.g., Sun et al. (2012) "Direct-Write Assembly of 3D Silk/Hydroxyapatite Scaffolds for Bone Co-Cultures." Advanced Healthcare Materials, no. 1: 729-735; Shepherd et al. (2011) "3D Microperiodic Hydrogel Scaffolds for Robust Neuronal Cultures." Advanced Functional Materials 21: 47-54; and Barry III et al. (2009) "Direct-Write Assembly of 3D Hydrogel Scaffolds for Guided Cell Growth." Advanced Materials 21: 1-4, for examples of a 3D biopolymer scaffold or mesh that can be used as a membrane in the device described herein.

In some embodiments, a membrane can comprise an elastomeric portion fabricated from a styrenic block copolymer-comprising composition, e.g., as described in the International Pat. App. No. PCT/US2014/071611, can be adopted in the devices described herein, the contents of each of which are incorporated herein by reference in its entirety. In some embodiments, the styrenic block copolymer-comprising composition can comprise SEBS and polypropylene.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

The pores of the membrane (including pore apertures extending through the membrane 208 from the top 208A to bottom 208B surfaces thereof and/or a connected network of void space within the membrane 208) can have a cross-section of any size and/or shape. For example, the pores can have a pentagonal, circular, hexagonal, square, elliptical, oval, diamond, and/or triangular shape.

The cross-section of the pores can have any width dimension provided that they permit desired molecules and/or cells to pass through the membrane. In some embodiments, the pore size of the membrane should be big enough to provide the cells sufficient access to nutrients present in a fluid medium flowing through the first chamber and/or the second chamber. In some embodiments, the pore size can be selected to permit passage of cells (e.g., immune cells and/or cancer cells) from one side of the membrane to the other. In some embodiments, the pore size can be selected to permit passage of nutrient molecules. In some embodiments, the width dimension of the pores can be selected to permit molecules, particulates and/or fluids to pass through the membrane 208 but prevent cells from passing through the membrane 208. In some embodiments, the width dimension of the pores can be selected to permit cells, molecules, particulates and/or fluids to pass through the membrane 208. Thus, the width dimension of the pores can be selected, in part, based on the sizes of the cells, molecules, and/or particulates of interest. In some embodiments, the width dimension of the pores (e.g., diameter of circular pores) can be in the range of 0.01 microns and 20 microns, or in one embodiment, approximately 0.1-15 microns, or approximately 1-10 microns. In one embodiment, the pores have a width of about 7 microns.

In an embodiment, the porous membrane 208 can be designed or surface patterned to include micro and/or nanoscopic patterns therein such as grooves and ridges, whereby any parameter or characteristic of the patterns can be designed to desired sizes, shapes, thicknesses, filling materials, and the like.

The membrane 208 can have any thickness to suit the needs of a target application. In some embodiments, the membrane can be configured to deform in a manner (e.g., stretching, retracting, compressing, twisting and/or waving) that simulates a physiological strain experienced by the cells in its native microenvironment. In these embodiments, a thinner membrane can provide more flexibility. In some embodiments, the membrane can be configured to provide a supporting structure to permit growth of a defined layer of cells thereon. Thus, in some embodiments, a thicker membrane can provide a greater mechanical support. In some embodiments, the thickness of the membrane 208 can range between 70 nanometers and 100 or between 1 μm and 100 μm, or between 10 and 100 μm. In one embodiment, the thickness of the membrane 208 can range between 10 μm and 80 μm. In one embodiment, the thickness of the membrane 208 can range between 30 μm and 80 μm. In one embodiment, the thickness of the membrane 208 can be about 50 μm.

While the membrane 208 generally have a uniform thickness across the entire length or width, in some embodiments, the membrane 208 can be designed to include regions which have lesser or greater thicknesses than other regions in the membrane 208. The decreased thickness area(s) can run along the entire length or width of the membrane 208 or can alternatively be located at only certain locations of the membrane 208. The decreased thickness area can be present along the bottom surface of the membrane 208 (i.e. facing second chamber 206), or additionally/alternatively be on the opposing surface of the membrane 208 (i.e. facing second chamber 204). It should also be noted that at least portions of the membrane 208 can have one or more larger thickness areas relative to the rest of the membrane, and capable of having the same alternatives as the decreased thickness areas described above.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In an embodiment, the cell attachment-promoting substances, matrix-forming formulations, and other compositions of matter are sterilized to prevent unwanted contamination. Sterilization can be accomplished, for example, by ultraviolet light, filtration, gas plasma, ozone, ethylene oxide, and/or heat. Antibiotics can also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In some embodiments, the membrane and/or other components of the devices described herein can be treated using gas plasma, charged particles, ultraviolet light, ozone, or any combinations thereof Using the devices described herein, one can study biotransformation, absorption, as well as drug clearance, metabolism, delivery, and toxicity. The activation of xenobiotics can also be studied. The bioavailability and transport of chemical and biological agents across epithelial layers as in a tissue or organ, e.g., parenchyma, and endothelial layers as in blood vessels, and across the proximal tubule cells and/or endothelial cells for drug metabolism can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be detected and studied using the devices described herein. The impact of genetic content on response to the agents can be studied. The amount of protein and gene expression in response to chemical or biological agents can be determined. Changes in metabolism in response to chemical or biological agents can be studied as well using devices described herein.

In some embodiments, the devices described herein (e.g., a Proximal Tubule-Chip) can be used to assess the clearance of a test compound. For clearance studies, the disappearance of a test compound can be measured (e.g. using mass spec) in the media of the top chamber, bottom chamber, or both chambers (divided by a membrane comprising Proximal Tubule cells).

For example, in accordance with one aspect of the invention, a Proximal Tubule-Chip drug-metabolizing performance can be measured by i) disposing a substrate compound with known blood or kidney metabolites in the media of the top chamber, bottom chamber, or both chambers; and ii) measuring the amount of generated metabolite in the media of the top chamber, bottom chamber or both chambers (e.g. using mass spec). As is known in the art, the choice of the substrate and measured metabolite can help provide information on specific kidney drug-metabolism enzymes (e.g. CYP450 isoforms, CYP 2B6 and 3A5, Non-CYP Enzymes, etc.)

In some embodiments, the devices described herein (e.g., a Proximal Tubule-Chip) can be used to assess the induction or inhibition potential of a test compound. For induction or inhibition studies a variety of tests are contemplated. For example, induction of a transporter or drug metabolism enzyme in the kidney may cause a drug-drug interaction leading to unwanted side-effects (toxicity); a change the efficacy of a drug or renal failure. A reliable and practical CYP3A induction assay with human hepatocytes in a 96-well format has been reported, where various 96-well plates with different basement membranes were evaluated using prototypical inducers, rifampicin, phenytoin, and carbamazepine. See Drug Metab. Dispo. (2010) November; 38(11):1912-6.

According to one aspect of the invention, the induction or inhibition potential of a test compound at a test concentration can be evaluated by i) disposing the test compound in the media of the top chamber, bottom chamber or both chambers at the test concentration; ii) exposing the device for a selected period of time; and iii) assessing the induction or inhibition of kidney enzymes by comparing proximal kidney cell performance to a measurement performed before the test compound was applied, to a measurement performed on a Proximal Tubule-on-Chip that was subjected to a lower concentration of test compound (or no test compound at all), or both. In some embodiments, the proximal kidney cell performance measurement can comprise an RNA expression level. In some embodiments, the proximal kidney cell performance measurement comprises assessing albumin release. In some embodiments, the proximal kidney cell performance measurement comprises assessing albumin resportion. In some embodiments, the proximal kidney cell performance measurement comprises assessing drug transporter function. In some embodiments, the proximal kidney cell performance measurement comprises assessing drug-metabolizing capacity.

In some embodiments, the devices described herein (e.g., a Proximal Tubule-Chip) can be used to identify in vivo metabolites of a test compound or agent, and optionally the in vivo ratio of these metabolites. According to one aspect of the invention, in vivo metabolites can be identified by i) disposing a test compound or agent in the media of the top chamber, bottom chamber, or both chambers; and ii) measuring the concentration of metabolites in the media of the top chamber, bottom chamber, or both chambers. In some embodiments, the measuring of the concentration of metabolites comprises mass spectroscopy.

In some embodiments, the devices described herein (e.g., a Proximal Tubule-Chip) can be used to identify the toxicity of a test compound or agent at a test concentration. According to one aspect of the invention, toxicity can be evaluated by i) disposing a test compound in the media of the top chamber, bottom chamber, or both chambers; and ii) measuring one or more toxicity endpoints selected from the list of leakage of cellular enzymes (e.g., lactose dehydrogenase, alanine aminotransferase, aspartate aminotransferase) or material (e.g., adenosine triphosphate), variation in RNA expression, inhibition of drug-metabolism capacity, reduction of intracellular ATP (adenosine triphosphate), cell death, apoptosis, and cell membrane degradation.

Exemplary Methods of Making the Devices Described Herein.

Embodiments of various devices comprising a first chamber, a second chamber, and a membrane can enable us to leverage the control of microfluidic technology for device fabrication. In some embodiments, the devices described herein can be manufactured using any conventional fabrication methods, including, e.g., injection molding, embossing, etching, casting, machining, stamping, lamination, photolithography, or any combinations thereof. Soft lithography techniques are described in "Soft Lithography in Biology and Biochemistry," by Whitesides, et al., published Annual Review, Biomed Engineering, 3.335-3.373 (2001), as well as "An Ultra-Thin PDMS Membrane As A Bio/Micro-Nano Interface: Fabrication And Characterization", by Thangawng et al., Biomed Microdevices, vol. 9, num. 4, 2007, p. 587-95, both of which are hereby incorporated by reference.

Without wishing to be limiting, in some embodiments, the devices described herein can be produced as a monolithic device or as individual components (e.g., a first structure comprising a first chamber, a second structure comprising a second chamber, and a membrane), which can then be assembled together to form a device described herein. Each individual component can be produced by a conventional manufacturing method such as injection molding, extrusion, casting, lamination, embossing, compression molding, solvent casting, an additive manufacturing method (e.g., 3D printing), or any combinations thereof.

Once the first and second structures 204, 206 are formed and removed from their respective molds, the access ports can be made to access the chambers.

The membrane 208 can be engineered for a variety of purposes, some discussed above.

In some embodiments, the membrane 208 can be sandwiched between the first structure and the second structure, e.g., using an appropriate adhesive or epoxy, physical clamping and/or plasma bond between the two PDMS surfaces, in order to form a fluidic seal between the membrane with the first structure and the second structure.

After forming the body of the devices described herein, the first side of the membrane can be coated with an ECM composition according to one or more embodiments described herein. After formation of the ECM composition, tissue specific cells, e.g., hepatocytes, can be grown thereon.

In some embodiments, at least one layer of cells comprising blood vessel-associated cells (e.g., fibroblasts, smooth muscle cells, and/or endothelial cells) can be cultured on the second side of the membrane.

A. Closed Top Microfluidic Chips Without Gels.

In one embodiment, closed top gut-on-chips, or other type of organ-chip, do not contain gels, either as a bulk gel or a gel layer. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips With Gels.

In one embodiment, closed top gut-on-chips do contain gels, such as a gel layer, or bulk gel, including but not limited to a gel matrix, hydrogel, etc. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips With Simulated Lumens.

A closed top gut-on-chip comprising a gel-lined simulated lumen may be used for generating a more physiological relevant model of gastrointestinal tissue. In some embodiments, closed top gut-on-chips further comprise a gel simulated three-dimensional (3-D) lumen. In other words, a 3-D lumen may be formed using gels by providing simulated intestinal villi (e.g. viscous fingers) and/or mimicking intestinal folds. In a preferred embodiment, the gel forms a lumen, i.e. by viscous fingering patterning.

Using viscous fingering techniques, e.g. viscous fingering patterning, a simulated intestinal lumen may be formed by numerous simulated intestinal villi structures. Intestinal villi (singular: villus) refer to small, finger-like projections that extend into the lumen of the small intestine. For example, healthy small intestine mucosa contains these small finger-like projections of tissue that are present along the lumen as folds of circular plica finger-like structures. A villus is lined on the luminal side by an epithelia cell layer, where the microvillus of the epithelial cells (enterocytes) faces the lumen (i.e. apical side). Viscous fingers may be long and broad, for mimicking villi in the duodenum of the small intestine, while thinner or shorter viscous fingers may be used for mimicking villi in other parts of the gastrointestinal tract. As one example, viscous fingers may be formed and used to mimic epithelial projections in the colon.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning." J Lab Autom. 2012 April; 17(2): 96-103, Author manuscript; available in PMC 2012 Jul. 16, herein incorporated by reference in its entirety. In one example of a viscous finger patterning method for use with microfluidic gut-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium.

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated intestinal villus.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular microenvironment, (e.g. MATRIGEL®. In some embodiments, the first and second permeable matrixes can each independently comprise a polymer matrix. Methods to create a permeable polymer matrix are known in the art, including, e.g. but not limited to, particle leaching from suspensions in a polymer solution, solvent evaporation from a polymer solution, sold-liquid phase separation, liquid-liquid phase separation, etching of specific "block domains" in block co-polymers, phase separation to block-co-polymers, chemically cross-linked polymer networks with defined permabilities, and a combination of two or more thereof.

Another example for making branched structures using fluids with differing viscosities is described in "Method And System For Integrating Branched Structures In Materials" to Katrycz, Publication number US20160243738, herein incorporated by reference in its entirety.

Regardless of the type of lumen formed by a gel and/or structure, cells can be attached to these structures either to lumen side of the gel and/or within the gel and/or on the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Microfluidic Chips.

Figure 2A:
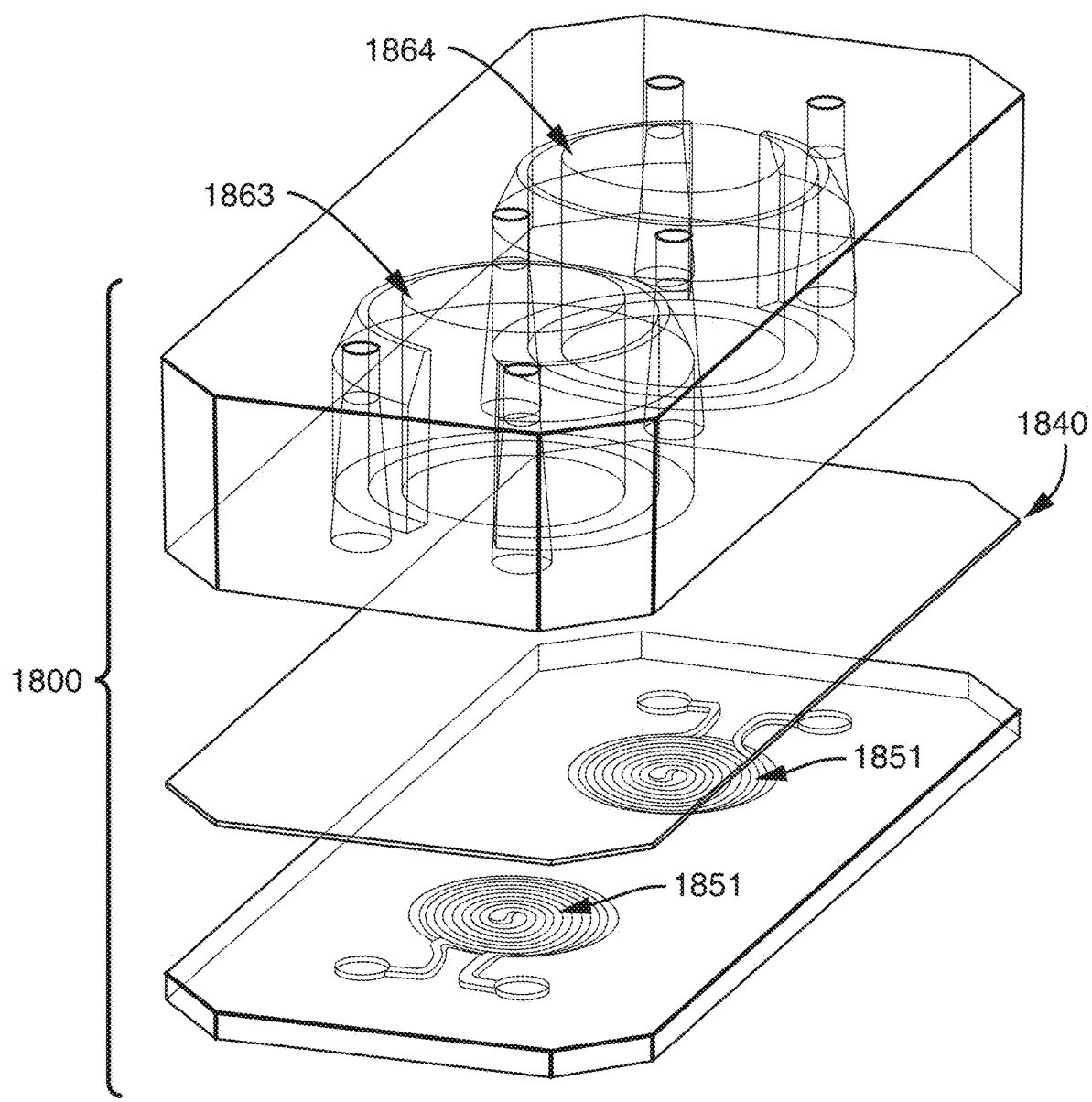
FIG. 2A shows one exemplary schematic of an open top microfluidic chip.
Figure 2B:
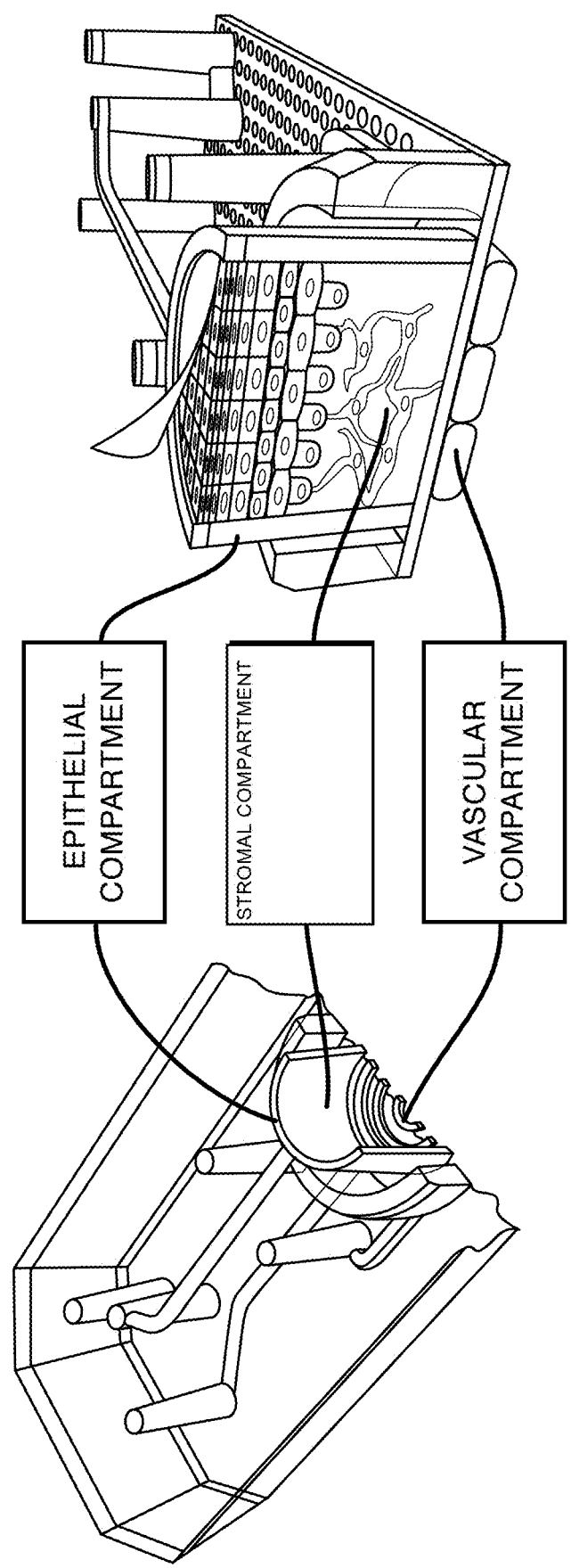
FIG. 2B shows two exemplary schematic embodiments of an open top microfluidic chip modeling a simulated kidney organ comprising kidney epithelium. One embodiment is a schematic of a partial open top chip demonstrating channels and open stromal area in relation to cellular compartments in the chip (left). One embodiment is a schematic of a partial open top chip additionally demonstrating cells in the compartments of the chip (right).

The present disclosure relates to gut-on-chips, such as fluidic devices comprising one or more cells types for the simulation one or more of the function of gastrointestinal tract components. Accordingly, the present disclosure additionally describes open-top gut-on-chips, see, e.g. schematic in FIG. 2A-B. FIG. 2A shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment can apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

A. Open Top Microfluidic Chips Without Gels.

In one embodiment, open top gut-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips With Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic chips comprise lumens formed by viscous fingering described herein for closed top chips.

Lumen gel structures may be used in several types of embodiments for open top microfluidic chips, e.g. epithelial cells or parenchymal cells can be attached to outside of the gel, or within the gel. In some embodiments, stromal cells are added within the gel. In some embodiments, stromal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels, with or without gels.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

IV. Chip Activation.

Open-Top Organ-Chip platform was chemically activated by sulfu sampo/buffer, such as HEPES, treatment (Emulate, Inc). Briefly, sulfu sampo and buffer were mixed together as specified by the instructions and added to the bottom spiraled shaped microfluidic channel and circular stromal chamber. The platform was then UV treated for 20 minutes using UV oven (e.g. 365 nm light and the bulb that generate the UV light are 9 Watt).

A. Chip Activation Compounds.

In one embodiment, bifunctional crosslinkers are used to attach one or more extracellular matrix (ECM) proteins. A variety of such crosslinkers are available commercially, including (but not limited to) the following compounds:

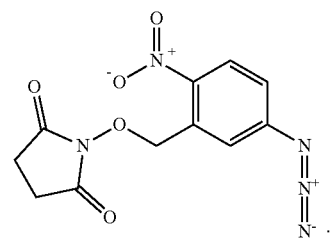

ANB-NOS
(N-5-azido-2-nitrobenzoyloxysuccinimide)

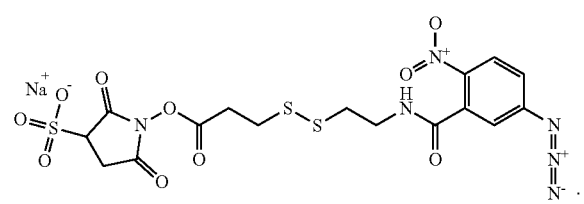

Sulfo-SAND
(sulfosuccinimidyl 2-
[m-azido-o-nitrobenzamido]ethyl-1,3'-
dithiopropionate)

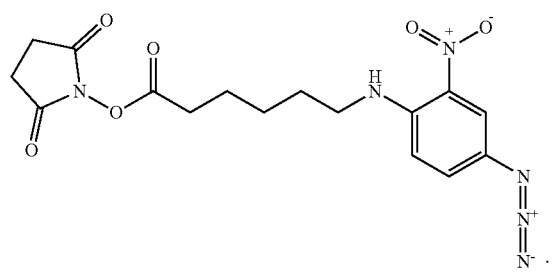

SANPAH
(N-succinimidyl-6-
[4'-azido-2'-nitrophenylamino]hexanoate)

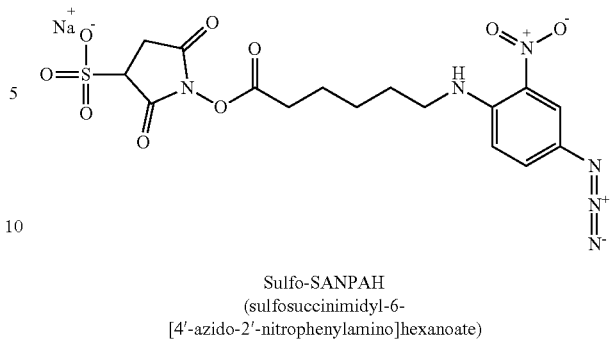

Sulfo-SANPAH
(sulfosuccinimidyl-6-
[4'-azido-2'-nitrophenylamino]hexanoate)

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups ($-NH_2$) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary methods of Chip Activation.
1. Prepare and sanitize hood working space
2. S-1 Chip Handling—Use aseptic technique, hold Chip using Carrier
   a. Use 70% ethanol spray and wipe the exterior of Chip package prior to bringing into hood
   b. Open package inside hood
   c. Remove Chip and place in sterile Petri dish (6 Chips/Dish)
   d. Label Chips and Dish with respective condition and Lot #
3. Surface Activation with Chip Activation Compound (light and time sensitive)
   a. Turn off light in biosafety hood
   b. Allow vial of Chip Activation Compound powder to fully equilibrate to ambient temperature (to prevent condensation inside the storage container, as reagent is moisture sensitive)
   c. Reconstitute the Chip Activation Compound powder with ER-2 solution
      i. Add 10 ml Buffer, such as HEPES, into a 15 ml conical covered with foil ii. Take 1 ml Buffer from above conical and add to chip Activation Compound (5 mg) bottle, pipette up and down to mix thoroughly and transfer to same conical
iii. Repeat 3-5 times until chip Activation Compound is fully mixed
iv. NOTE: Chip Activation Compound is single use only, discard immediately after finishing Chip activation, solution cannot be reused
d. Wash channels
  i. Inject 200 µl of 70% ethanol into each channel and aspirate to remove all fluid from both channels
  ii. Inject 200 µl of Cell Culture Grade Water into each channel and aspirate to remove all fluid from both channels
  iii. Inject 200 µl of Buffer into each channel and aspirate to remove fluid from both channels
e. Inject Chip Activation Compound Solution (in buffer) in both channels
  i. Use a P200 and pipette 200 µl to inject Chip Activation Compound/Buffer into each channel of each chip (200 µl should fill about 3 Chips (Both Channels))
  ii. Inspect channels by eye to be sure no bubbles are present. If bubbles are present, flush channel with Chip Activation Compound/Buffer until bubbles have been removed
f. UV light activation of Chip Activation Compound Place Chips into UV light box
  i. UV light treat Chips for 20 minutes.
  ii. While the Chips are being treated, prepare ECM Solution.
  iii. After UV treatment, gently aspirate Chip Activation Compound/Buffer from channels via same ports until channels are free of solution
  iv. Carefully wash with 200 µl of Buffer solution through both channels and aspirate to remove all fluid from both channels
  v. Carefully wash with 200 µl of sterile DPBS through both channels
  vi. Carefully aspirate PBS from channels and move on to: ECM-to-Chip VI. ECM-to-Chip
A. Calculate total volume of ECM solution needed to coat Chips or hydrogel surfaces, these are exemplary ECM materials, as laminin may also be used with one or more ECM materials.
  1. Volume required per Chip=50 ul/Channel
  2. ECM diluent: PBS, prepared on ice
  3. Stock Concentrations for ECM coating:
    a. Collagen IV: 1 mg/ml (200 µl aliquots in −20° C.)
    b. Fibronectin: 1 mg/ml (50 µl aliquots in 4° C.)
    c. Matrigel: 10 mg/ml (200 µl aliquots in −20° C.)
  4. Working Concentrations for ECM coating:
    a. Collagen IV: 200 µg/ml
    b. Fibronectin: 30 µg/ml
  5. Top Channel Coating: 50 µl Collagen IV (200 µg/ml) and Matrigel (100 µg/ml)
  6. Bottom Channel Coating: 50 µl Collagen IV (200 µg/ml) and Fibronectin (30 ug/ml)
B. Load Channels with ECM solution.
  1. Place Chips in hood
  2. Pipette 50 µl of Top Channel Coating into Top Channel—keep the pipette plunger depressed until you see fluid come out opposite end of the channel, then take another pipette tip (200 µl tip) to close the outlet port. Once closed off, carefully remove the pipette tip, leaving the tip in the inlet port.
  3. Aspirate excess fluid from the surface of Chip (avoid direct contact with the port)
  4. Repeat 2b-2c, but with Bottom Channel Coating into Bottom Channel
  5. Incubate at 37° C. for a minimum of 2 hours up to overnight
C. Exemplary Matrigel Coating
  1. Thaw Matrigel on ice and keep chilled to prevent solidification.
  2. Prepare Matrigel
    a. Matrigel Stock Concentration: 10 mg/ml
    b. Matrigel Final Concentration: 250 µg/ml
    c. Determine the volume of Matrigel needed to coat 50 µl of each Top Channel and resuspend accordingly in cell culture media
    d. Transfer the seeded Chips into the hood
    e. Wash both channels of each chip twice with 200 µl media
    f. Before inserting the tips, add a drop of media to prevent formation of bubbles
    g. Leave 50 ul media in bottom channel (Tips inserted)
    h. Add 50 l 250 ug/ml Matrigel to top channel (Tips inserted)
    i. Incubate at 37° C. overnight.
V. Cells-to-Chip-Chip Preparation.
1. Transfer the ECM coated Chips into the hood
  a. Gently wash Chips after ECM coating
2. Pipette 200 µl of DPBS into bottom channel inlet port—keep the pipette plunger depressed until you see fluid come out opposite end of channel and aspirate outflow
3. Repeat the same procedure to wash top channel
4. Pipette 200 µl of DPBS into top channel inlet port—keep the pipette plunger depressed until you see fluid come out opposite end of the channel, then take another pipette tip (200 µl) to close the outlet port. Once closed off, carefully remove the pipette tip, leaving the tip in the inlet port
5. Repeat the same with the bottom channel. Place back in incubator until cells are ready.

EXPERIMENTAL

Example: RNA (Gene) Expression Profiling

Gene expression profiling refers to measurement of the activity (expression) of thousands of genes at once, to create a global picture of cellular function. As one example, RNA-Seq (Illumina, Inc. 5200 Illumina Way, San Diego, Calif. 92122), provides information on the sequences of genes in addition to their expression level.

As one example, total RNA can be extracted and used to generate biotin-labeled cRNA, e.g. using an Illumina TotalPrep RNA Amplification Kit (Ambion, Austin, Tex.). Biotin-labeled cRNA was then hybridized to Illumina HumanHT-12 whole genome expression beadchips (Illumina, San Diego, Calif.). The quality of the Illumina bead summary data can be assessed using the Bioconductor package Lumi. Data preprocessing may include variance stabilization and quantile normalization. To eliminate potentially confounding effects of RNA quality on gene expression, residuals may be calculated from the regression analysis of RIN values on gene expression and used for statistical analysis and WGCNA network construction. Outlier values may then be removed for each gene within a group using Grubbs' test (p<0.05). Statistical analysis comparing alcoholic and control groups may be performed using the Bioconductor package Limma to carry out a Bayesian two-tailed t-test. A false discovery rate (FDR) for each list of significantly regulated genes with nominal P values<0.05 may be estimated using the method of Benjamini and Hochberg (1995). Our systems approach to prioritizing individual genes may be based on integration of nominal statistical significance, gene network information and functional relevance. Therefore, to avoid omitting true positives, all genes with nominal P values <0.05 may be considered.

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The invention claimed is:

1. A method of culturing, comprising:
   a) providing a microfluidic device comprising a membrane, said membrane comprising a first surface and a second surface, said first surface comprising proximal tubule cells and said second surface comprising glomerular microvascular endothelial cells;
   b) exposing said proximal tubule cells and said glomerular microvascular endothelial cells to media under continuous low shear flow; and
   c) culturing said proximal tubule cells such that said proximal tubule cells express aqua porin 1 (AQP1) with at least two-fold greater relative gene expression as compared to the same proximal tubule cells cultured in a static culture.

2. The method of claim 1, wherein said proximal tubule cells are human primary proximal tubular epithelial cells.

3. The method of claim 2, wherein said membrane contains pores.

4. The method of claim 3, wherein said human primary proximal tubular epithelial cells are attached to the top of said membrane and said glomerular microvascular endothelial cells are attached to the opposite side of the same membrane.

5. The method of claim 1, wherein said first surface of said membrane is part of a first microfluidic channel and said second surface of said membrane is part of a second microfluidic channel.

6. The method of claim 2, wherein said human primary proximal tubular epithelial cells express tight junction protein ZO-1.

7. The method of claim 2, wherein said human primary proximal tubular epithelial cells express beta-catenin.

8. The method of claim 2, wherein said human primary proximal tubular epithelial cells express occludin.

9. The method of claim 2, wherein said human primary proximal tubular epithelial cells express Na/K-ATPase.

10. The method of claim 2, wherein said human primary proximal tubular epithelial cells comprise cilia.

11. The method of claim 2, wherein said human primary proximal tubular epithelial cells express one or more uptake and efflux transporters.

12. The method of claim 2, wherein said continuous flow of media is 30 µl/hr.

13. The method of claim 2, wherein said continuous flow of media is 150 µl/hr.

14. The method of claim 2, wherein said human primary proximal tubular epithelial cells express aquaporin 1 (AQP1) with at least four-fold greater relative gene expression as compared to the same human primary proximal tubular epithelial cells cultured in a static culture.

15. The method of claim 2, wherein said human primary proximal tubular epithelial cells express aquaporin 1 (AQP1) with at least ten-fold greater relative gene expression as compared to the same human primary proximal tubular epithelial cells cultured in a static culture.

16. A method of culturing, comprising:
   a) providing a microfluidic device comprising a membrane, said membrane comprising a first surface and a second surface, said first surface comprising human primary proximal tubular epithelial cells and said second surface comprising glomerular microvascular endothelial cells;
   b) culturing said human primary proximal tubular epithelial cells and said glomerular microvascular endothelial cells to media under continuous low shear flow such that said human primary proximal tubular epithelial cells express beta-catenin; and
   c) detecting said human primary proximal tubular epithelial cells expressing beta-catenin.

17. A method of culturing, comprising:
   a) providing a microfluidic device comprising a membrane, said membrane comprising a first surface and a second surface, said first surface comprising human primary proximal tubular epithelial cells and said second surface comprising glomerular microvascular endothelial cells;
   b) culturing said human primary proximal tubular epithelial cells and said glomerular microvascular endothelial cells to media under continuous low shear flow such that said human primary proximal tubular epithelial cells express occludin; and
   c) detecting said human primary proximal tubular epithelial cells expressing occludin.

* * * * *